United States Patent
Stupp et al.

(10) Patent No.: US 11,964,000 B2
(45) Date of Patent: Apr. 23, 2024

(54) CANCER TREATMENT METHODS USING NANOFIBER STABILIZED GROWTH FACTORS

(71) Applicant: Northwestern University, Evanston, IL (US)

(72) Inventors: Samuel I. Stupp, Chicago, IL (US); Mark Trosper McClendon, Chicago, IL (US); Guifa Xi, Chicago, IL (US); Bo Timmy Bjoern Fyrner, Kopparberg (SE); Cara S. Smith, Chicago, IL (US); Nicholas A. Sather, Evanston, IL (US)

(73) Assignee: Northwestern University, Evanston, IL (US)

( * ) Notice: Subject to any disclaimer, the term of this patent is extended or adjusted under 35 U.S.C. 154(b) by 30 days.

(21) Appl. No.: 17/227,943

(22) Filed: Apr. 12, 2021

(65) Prior Publication Data
US 2021/0315972 A1  Oct. 14, 2021

Related U.S. Application Data

(60) Provisional application No. 63/008,290, filed on Apr. 10, 2020.

(51) Int. Cl.
| | | |
|---|---|---|
| A61K 38/18 | (2006.01) | |
| A61K 45/06 | (2006.01) | |
| A61K 47/54 | (2017.01) | |
| A61K 47/61 | (2017.01) | |
| A61K 47/64 | (2017.01) | |
| A61P 35/00 | (2006.01) | |

(52) U.S. Cl.
CPC .......... *A61K 38/1875* (2013.01); *A61K 45/06* (2013.01); *A61K 47/549* (2017.08); *A61K 47/61* (2017.08); *A61K 47/641* (2017.08); *A61K 47/645* (2017.08); *A61P 35/00* (2018.01)

(58) Field of Classification Search
None
See application file for complete search history.

(56) References Cited

U.S. PATENT DOCUMENTS

| | | |
|---|---|---|
| 6,890,654 B2 | 5/2005 | Stupp et al. |
| 7,371,719 B2 | 5/2008 | Stupp et al. |
| 7,390,526 B2 | 6/2008 | Stupp et al. |
| 7,452,679 B2 | 11/2008 | Stupp et al. |
| 7,491,690 B2 | 2/2009 | Stupp et al. |
| 7,534,761 B1 | 5/2009 | Stupp et al. |
| 7,544,661 B2 | 6/2009 | Stupp et al. |
| 7,554,021 B2 | 6/2009 | Stupp et al. |
| 7,683,025 B2 | 3/2010 | Stupp et al. |
| 7,745,708 B2 | 6/2010 | Stupp et al. |
| 7,838,491 B2 | 11/2010 | Stupp et al. |
| 7,851,445 B2 | 12/2010 | Stupp et al. |
| 8,063,014 B2 | 11/2011 | Stupp et al. |
| 8,080,262 B2 | 12/2011 | Lee et al. |
| 8,114,834 B2 | 2/2012 | Hsu et al. |
| 8,114,835 B2 | 2/2012 | Mata et al. |
| 8,124,583 B2 | 2/2012 | Stupp et al. |
| 8,138,140 B2 | 3/2012 | Stupp et al. |
| 8,450,271 B2 | 5/2013 | Shah et al. |
| 8,512,693 B2 | 8/2013 | Capito et al. |
| 2018/0125924 A1 | 5/2018 | Stupp et al. |

OTHER PUBLICATIONS

National Cancer Institute (https://www.cancer.gov/about-cancer/understanding accessed Dec. 29, 2022).*
Xi et al. ("Therapeutic Potential for Bone Morphogenetic Protein 4 in Human Malignant Glioma" Neoplasia Apr. 2017: 19(4): 261-270).*
Deng et al. ("BMP4 promotes hepatocellular carcinoma proliferation by autophagy activation through JNK-1 mediated BCL-2 phosphorylation" Journal of Experimental & Clinical Cancer Research 2018 37:156).*
Yang et al. ("The correlation of bone morphogenetic protein 2 with poor prognosis in glioma patients" Tumor Biology 35, 11091-11095 (2014).*
Israelachvili, J. N. Intermolecular and surface forces; 2nd ed.; Academic: London San Diego, 1992.
Mayo, K.H et al. A recipe for designing water-soluble, β-sheet-forming peptides. Protein Science, 1996; 5(7); 1301-1315.

* cited by examiner

*Primary Examiner* — Julie Ha
*Assistant Examiner* — Tara L Martinez
(74) *Attorney, Agent, or Firm* — Casimir Jones, S.C.; Rikki A. Hullinger

(57) ABSTRACT

Provided herein are compositions comprising peptide amphiphiles, glycosylated peptide amphiphiles (GPAs), supramolecular nanostructures assembled therefrom, and methods of use thereof. The peptide amphiphiles described herein may extend the half-life of bone morphogenic proteins, promote cell differentiation, suppress proliferation, and increase chemosensitivity of cells. Accordingly, the compositions described herein may be used for cancer treatment methods. In particular, provided herein are bone morphogenic proteins bound to peptide amphiphiles and glycosylated peptide amphiphiles or composites thereof, and methods of use of the same for the treatment of cancer. Also, provided herein are bone morphogenic proteins bound to peptide amphiphiles and glycosylated peptide amphiphiles or composites thereof, and methods of use of the same in a combinatorial approach together with chemotherapeutic medications for the treatment of cancer.

11 Claims, 26 Drawing Sheets
Specification includes a Sequence Listing.

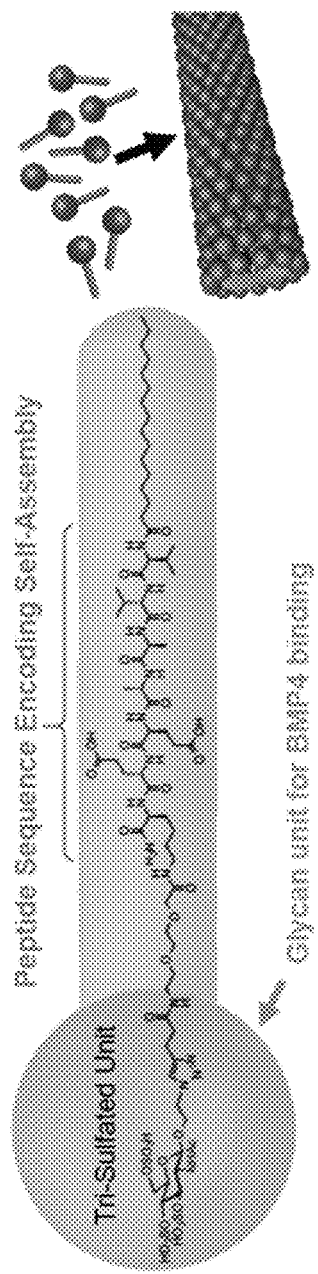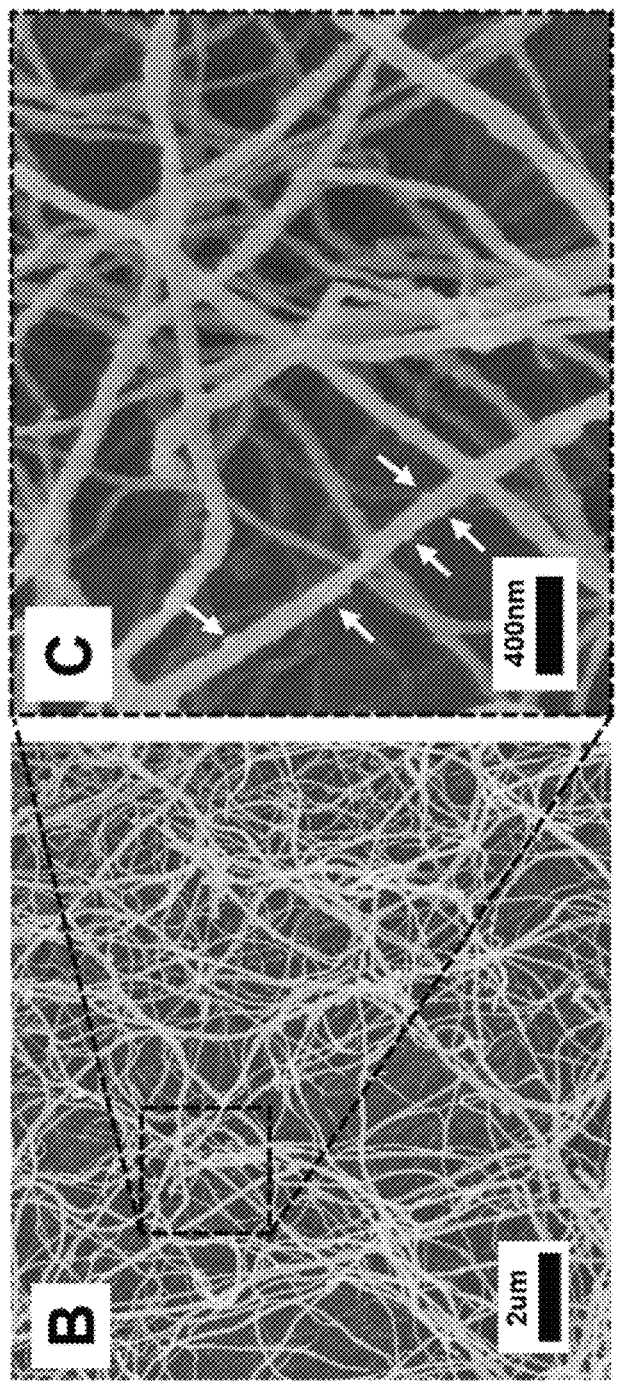
FIG. 3A
FIG. 3B
FIG. 3C

CANCER TREATMENT METHODS USING NANOFIBER STABILIZED GROWTH FACTORS

STATEMENT REGARDING RELATED APPLICATIONS

This application claims priority to U.S. Provisional Patent Application No. 63/008,290, filed Apr. 10, 2020, the entire contents of which are incorporated herein by reference for all purposes.

STATEMENT REGARDING FEDERALLY SPONSORED RESEARCH OR DEVELOPMENT

This invention was made with government support under grant number P50CA221747-O1A1 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 776 Byte ASCII (Text) file named "2021-04-12_38387-202_SQL_ST25.txt," created on Apr. 12, 2021.

FIELD

Provided herein are bone morphogenic proteins bound to peptide amphiphiles and methods of use thereof. In particular, provided herein are bone morphogenic proteins bound to peptide amphiphiles, and methods of use of the same for the treatment of cancer. In some aspects, provided herein are bone morphogenic proteins bound to peptide amphiphiles for use in combination with chemotherapy or other suitable cancer treatment methods.

BACKGROUND

Pediatric high-grade glioma (HGG) is among the most formidable cancer occurring in childhood. Gross total surgical resection with subsequent chemo- and radiation therapy has proven non-curative in nearly all instances. Bone morphogenetic protein 4 (BMP4) induces apoptosis and in so doing also increases cell sensitivity to cytotoxic therapies. Higher levels of intratumoral BMP4 have been associated with a more favorable prognosis for various cancers, consistent with the concept that treating tumors with exogenous BMP4 could prove effective in various types of cancer. However, attempts to treat HGG using BMP4 have been largely unsuccessful due to its short half-life. Accordingly, there is a clear need for delivery systems that can extend the half-life of BMP4 or other suitable cancer therapies in vivo.

SUMMARY

In some aspects, provided herein are methods of treating cancer in a subject. In some embodiments, the methods comprise providing to the subject a composition a composition containing a plurality of glycosylated peptide amphiphiles (GPAs) and a bone morphogenic proteins. In some embodiments, each GPA comprises a hydrophobic segment, a structural peptide segment, a charged peptide segment, and a terminal saccharide. In some embodiments, the plurality of GPAs are configured to form a self-assembled glyconanostructure, and the bone morphogenic protein binds to the surface of the glyconanostructure.

In some embodiments, the saccharide is selected from a monosaccharide, disaccharide, oligosaccharide, and a glycomimetic. In some embodiments, the saccharide is sulfated. In some embodiments, the saccharide is a monosaccharide, such as GlcA, GlcNAc, GlcNS, IdoA, Glc, Gal, Man, Tal, GlcN, GalNAc, GalNH$_2$, Fru, Neu5Ac, Fuc, Rha, Xyl, Rib, Ara, or sulfated versions thereof. In some embodiments, the saccharide is a disaccharide, such as a disaccharide of GlcA, GlcNAc, GlcNS, IdoA, Glc, Gal, Man, Tal, GlcN, GalNAc, GalNH$_2$, Fru, Neu5Ac, Fuc, Rha, Xyl, Rib, Ara, or sulfated versions thereof. In some embodiments, the saccharide is an oligosaccharide, such as an oligosaccharide of GlcA, GlcNAc, GlcNS, IdoA, Glc, Gal, Man, Tal, GlcN, GalNAc, GalNH$_2$, Fru, Neu5Ac, Fuc, Rha, Xyl, Rib, Ara, or sulfated versions thereof. Other suitable saccharides include, for example, glycomimetics, sulfated fucoidan disaccharides and oligosaccharides, and sugar alcohols and polyols.

In some embodiments, the saccharide is a monosaccharide, disaccharide, or oligosaccharide comprising a sulfated version of one of GlcA, GlcNAc, GlcNS, or IdoA. In some embodiments, the saccharide is a monosaccharide of GlcNAc(3,4,6S).

In some embodiments, the bone morphogenic protein is BMP-2 or BMP-4. For example, the bone morphogenic protein may be BMP-4.

In some embodiments, the composition further comprises one or more filler peptide amphiphiles (PAs). The filler PAs comprise a hydrophobic segment, a structural peptide segment, and a charged peptide segment, but lack a terminal saccharide. The filler peptide amphiphiles may be configured to incorporate into the glyconanostructure (e.g. the glyconanostructure containing the GPAs and the bone morphogenic protein).

In some embodiments, the composition further comprises a chemotherapeutic agent. In some embodiments, the chemotherapeutic agent is an alkylating agent. In some embodiments, the chemotherapeutic agent is an "alkylating-like" agent, such as a platinum derivative. In some embodiments, the chemotherapeutic agent comprises cisplatin (azane;dichloroplatinum). In some embodiments, the chemotherapeutic agent comprises carboplatin (azanide;cyclobutane-1,1-dicarboxylic acid;platinum(2+)).

In some embodiments, methods of treating cancer in a subject comprise providing to the subject a composition containing a plurality of peptide amphiphiles (PAs) and a bone morphogenic protein. The peptide amphiphiles comprise a hydrophobic segment, a structural peptide segment, and a charged peptide segment, but lack a terminal saccharide. In some embodiments, the plurality of PAs are configured to form a self-assembled nanostructure, and the bone morphogenic protein binds to the surface of the nanostructure. The bone morphogenic protein may be BMP-2 or BMP-4. For example, the bone morphogenic protein may be BMP-4.

The composition may further comprise a glycosylated peptide amphiphile (GPA) comprising a hydrophobic segment, a structural peptide segment, a charged peptide segment, and a terminal saccharide. In some embodiments, the composition further comprises a chemotherapeutic agent. In some embodiments, the composition may be administered to the subject in conjunction with a separate composition comprising a chemotherapeutic agent. In some embodiments, the chemotherapeutic agent is an alkylating agent. In some embodiments, the chemotherapeutic agent is an "alkylating-like" agent, such as a platinum derivative. In some embodiments, the chemotherapeutic agent comprises cisplatin (azane;dichloroplatinum). In some embodiments, the chemotherapeutic agent comprises carboplatin (azanide;cyclobutane-1,1-dicarboxylic acid;platinum(2+)). In such embodiments, the composition comprising the peptide amphiphile and the composition comprising the chemotherapeutic agent may be administered simultaneously or sequentially.

For any of the embodiments described herein, the cancer may be a brain cancer. For example, the cancer may be a pediatric high grade glioma. In some embodiments, the composition is provided to the subject intracranially. In some embodiments, the chemotherapeutic medication is provided systemically. In some embodiments, the composition is provided to the subject in combination with one or more additional cancer therapies selected from surgery, chemotherapy, radiation therapy, transplant, immunotherapy, hormone therapy, targeted drug therapy, cryoablation, and radiofrequency ablation. For example, the composition may be provided to the subject in combination with chemotherapy and/or radiation therapy.

BRIEF DESCRIPTION OF THE DRAWINGS

(FIG. 1A) H3K4me3 levels were visualized in pediatric low grade gliomas (pLGGs) (WHO grades I & II, n=51) and pHGGs (WHO grade III & IV, n=15) via immunohistochemistry (IHC) using H3K4me3 antibody. The results show H3K4me3 associates with WHO grade malignancy. (FIG. 1B) Quantitate IHC results for H3K4me3. (FIG. 1C) Survival analysis of pediatric gliomas correlates with H3K4me3 levels determined by IHC. (FIG. 1D, FIG. 1E) SETD1A expression in pediatric gliomas, associates with WHO grade, whereas SETD1B expression does not. (FIG. 1F) Protein expression of WDR82, hSETD1A and H3K4me3 in pediatric gliomas.

FIG. 2. BMP4 increases chemotherapeutic efficacy via reducing SETD1A and H3K4me3.

FIG. 3. BMP4 binding peptide amphiphile nanostructures extend half-life and enhance biological function of BMP4. (FIG. 3A) Molecular structure of GlncPA molecule (i.e. the glycosylated peptide amphiphile or "GPA") and schematic of the self-assembled GlncPA nanofiber. The grey molecular region guides the self-assembly process into nanofibers, the blue molecular region contains the tri-sulfated monosaccharide responsible for protein binding actions. (FIG. 3B) SEM of GlncPA nanofiber bundles after exposure to blood proteins for 5 minutes. (FIG. 3C) Higher magnification of nanofibers with white arrows indicating rigid surface texture resulting from proteins binding to the fiber surface.

FIG. 4. BMP4 binding peptide amphiphile nanostructures promote astrocyte differentiation and reduce proliferation.

FIG. 6. Glycosylated peptide amphiphile nanostructures spread to cover larger area in orthotopic xenograft intracranial tumor models.

FIG. 7. Glycosylated peptide amphiphile nanostructures decrease tumor growth in vivo in orthotopic xenograft intracranial tumor models.

FIG. 8. Glycosylated peptide amphiphile nanostructures enhance chemosensitivity and increase survival of SCID mice treated with chemotherapy drug.

DEFINITIONS

Figure 1A:
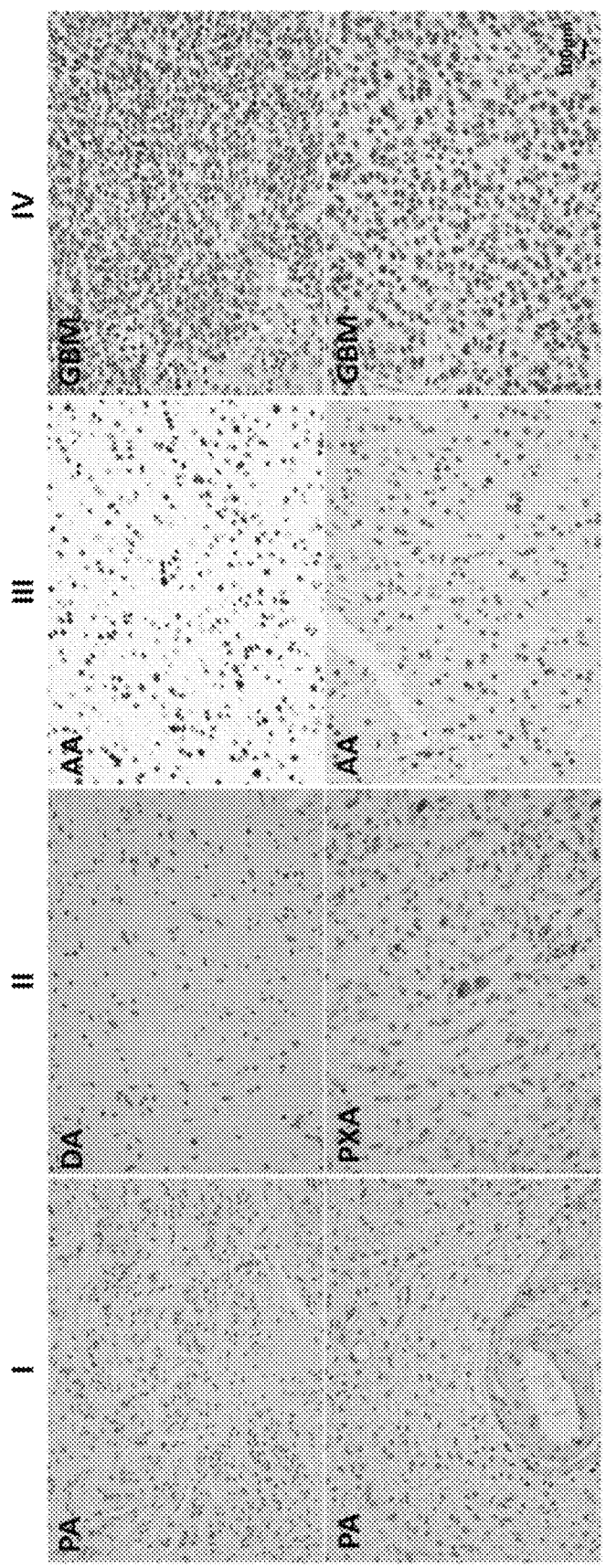
FIGS. 1A-F show that H3K4me3 and its methyltransferase SETD1A associate with pediatric glioma malignancy.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the terms "amino-rich peptide segment", "basic peptide segment," and "positively-charged peptide segment" refer to a peptide sequence of a peptide amphiphile that comprises one or more amino acid residues that have side chains displaying positively-charged acid side chains (e.g., Arg (R), Lys (K), His (H), or non-natural amino acids, desipeptides, or peptidomimetics). A basic peptide segment may optionally contain one or more additional (e.g., non-basic) amino acid residues. Non-natural amino acid residues with basic side chains could be used, as will be evident to one ordinarily skilled in the art. There may be from about 2 to about 7 amino acids, and or about 3 or 4 amino acids in this segment.

As used herein, the term "alkylating agent" refers to a chemotherapeutic agent that attaches an alkyl group to DNA, thereby damaging the DNA.

As used herein, the term "alkylating-like agent" refers to a chemotherapeutic agent that damages DNA, but do not have an alkyl group. In some embodiments, an alkylating-like agent is a platinum-based chemotherapeutic agent (e.g. a platinum derivative). Examples of platinum-based, alkylating-like agents include, for example, Cisplatin, Carboplatin, Dicycloplatin, Eptaplatin, Lobaplatin, Miriplatin, Nedaplatin, Oxaliplatin, Picoplatin, Satraplatin, and Triplatin tetranitrate.

As used herein, the term "artificial" refers to compositions and systems that are designed or prepared by man, and are not naturally occurring. For example, an artificial peptide, peptoid, or nucleic acid is one comprising a non-natural sequence (e.g., a peptide without 100% identity with a naturally-occurring protein or a fragment thereof).

As used herein, the term "bioisostere" refers to chemical substituents or functional groups that exhibit similar physicochemical properties and produce similar biological properties as the native functional group being mimicked. "Classical bioisosteres" are functional groups categorized as: monovalent atoms or groups, divalent atoms or groups, trivalent atoms or groups, tetravalent atoms and groups, and ring equivalents. "Non-classical bioisosteres" are counterparts that do not fulfill the steric and electronic criteria required for the "classical bioisosteres".

Examples of bioisosteres, are but not limited to: hydrogen and fluoride, deuterium and hydrogens, carboxylic acid and the tetrazole ring, carboxylic acid and acyl sulfonamide, carboxylic acid and aryl sulfonamide, amide and imidazole, amide and ester, amide and carbamate, amide and urea.

As used herein, the term "beta (p)-sheet-forming peptide segment" refers to a structural peptide segment that has a propensity to display β-sheet-like character (e.g., when analyzed by CD). In some embodiments, amino acids in a beta (p)-sheet-forming peptide segment are selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used. Peptide segments capable of interacting to form beta sheets and/or with a propensity to form beta sheets are understood (See, e.g., Mayo et al. Protein Science (1996), 5:1301-1315; herein incorporated by reference in its entirety).

As used herein, the term "charged peptide segment" refers to a portion of a peptide amphiphile that is rich (e.g., >50%, >75%, etc.) in charged amino acid residues (e.g. residues that have a net positive or negative charge under physiologic conditions). A charged peptide segment may be acidic (e.g., negatively charged), basic (e.g., positively charged), or zwitterionic (e.g., having both acidic and basic residues).

As used herein, the terms "carboxy-rich peptide segment," "acidic peptide segment," and "negatively-charged peptide segment" refer to a peptide sequence of a peptide amphiphile that comprises one or more amino acid residues that have side chains displaying carboxylic acid side chains (e.g., Glu (E), Asp (D), or non-natural amino acids). A carboxy-rich peptide segment may optionally contain one or more additional (e.g., non-acidic) amino acid residues. Non-natural amino acid residues, disipeptides, or peptidomimetics with acidic side chains could be used, as will be evident to one ordinarily skilled in the art. There may be from about 2 to about 7 amino acids, and or about 3 or 4 amino acids in this segment.

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "fucodian" or "sulfated fucodian" refers to sulfated di-, oligo-, or polysaccharides that have a backbone built of (1→3)-linked α-1-fucopyranosyl or of alternating (1→3)- and (1→4)-linked α-1-fucopyranosyl residues, but also include sulfated galactofucans with backbones built of (1→6)-β-d-galacto- and/or (1→2)-β-d-mannopyranosyl units with fucose or fuco-oligosaccharide branching, and/or glucuronic acid, xylose or glucose substitutions. There are at least two distinct forms of fucoidan: F-fucoidan, which is >95% composed of sulfated esters of fucose, and U-fucoidan, which is approximately 20% glucuronic acid.

As used herein, the term "glycosaminoglycan" (also referred to herein by the abbreviation "GAG") refers to a class of complex polysaccharides having repeating units of mono- or disaccharides. Non-limiting examples of glycosaminoglycans include dermatan sulfate, hyaluronic acid, the chondroitin sulfates, chitin, heparin, heparan sulfate, keratan sulfate, keratosulfate, and derivatives thereof.

As used herein, the term "glycosylated" refers to a compound, polymer, complex, etc. having a carbohydrate residue such as a monosaccharide, disaccharide, oligosaccharide, polysaccharide, sugar alcohol, polyol, or a glycomimetic appended to the reference compound, polymer, complex, etc. The term "glycopeptide" refers to a glycosylated peptide. For example, a "glycosylated peptide amphiphile" is a peptide amphiphile having a mono-, di-, oligo-, polysaccharide, or glycomimetic appended thereto.

As used herein, the term "glycomimetic" refers to molecular entities that exhibit structural and/or physical properties similar to carbohydrates and/or that exhibit similar or improved binding activity, biological activity, and/or stability.

Carbohydrate mimetics include, but are not limited to, aza-sugars, c-glycosides, carbasugars, thiosugars, thioglycosides, sulfosugars, iminosugars, phospha sugars, glycosylamines, lactones, pseudo-sugars, aminocyclitols, cyclitols, polyols, inositols such as myo-inositol and scyllo-inositols.

As used herein and in the appended claims, the term "lipophilic moiety" or "hydrophobic moiety" refers to the moiety disposed on one terminus disposed on one terminus (e.g., C-terminus, N-terminus) of the peptide amphiphile, and may be herein and elsewhere referred to as the lipophilic or hydrophobic segment or component. Any suitable hydrophobic segment may be used. In some embodiments, the hydrophobic segment is a hydrophobic peptide segment. In some embodiments, the hydrophobic segment is a non-peptide hydrophobic segment. In some embodiments, the hydrophobic segment comprises an acyl, ether, sulfonamide, or phosphodiester moiety. The hydrophobic segment should be of a sufficient length to provide amphiphilic behavior and aggregate (or nanosphere or nanofiber) formation in water or another polar solvent system. In some embodiments, the hydrophobic component comprises a single, linear acyl chain of the formula: $C_{n-1}H_{2n-1}C(O)$—where n=2-25. In some embodiments, a linear acyl chain is the lipophilic group (saturated or unsaturated carbons), palmitic acid. However, other lipophilic groups may be used in place of the acyl chain such as steroids, phospholipids and fluorocarbons.

As used herein, the term "mimetic" refers to a compound or complex which has substantially the same structural and/or functional characteristics as the reference molecule (e.g., binds to the protein). For example, "glycosaminoglycan mimetic" exhibits similar structural and/or functional (e.g., binds growth factors) features as glycosaminoglycans. As used herein, the term "peptidomimetic" refers to a peptide-mimicking or modulating pseudopeptidic sequence. Suitable peptidomimetics include, for example, peptoids, β-peptides, depsipeptides, hydrazinopeptides, and the like.

As used herein, the term "nanofiber" refers to an elongated or threadlike filament (e.g., having a significantly greater length dimension that width or diameter) with a diameter typically less than 100 nanometers. A nanofiber is an exemplary "nanostructure" described herein. A "nanostructure" is inclusive of a "glyconanostructure". The term "glyconanostructure" refers to a type of nanostructure containing at least one glycosylated peptide amphiphile.

As used herein, the term "peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "peptide amphiphile" refers to a molecule that, at a minimum, includes a hydrophobic segment, a structural peptide segment and/or charged peptide segment (often both), and optionally a functional segment (e.g., linker segment, bioactive segment, etc.). The peptide amphiphile may express a net charge at physiological pH, either a net positive or negative net charge, or may be zwitterionic (i.e., carrying both positive and negative charges). Certain peptide amphiphiles consist of or comprise: (1) a hydrophobic, non-peptide segment (e.g., comprising an acyl group of six or more carbons), (2) a structural peptide segment (e.g., (3-sheet forming); (3) a charged peptide segment, and (4) a functional segment (e.g., linker segment).

As used herein, the term "peptoid" refers to a class of peptidomimetics where the side chains are functionalized on the nitrogen atom of the peptide backbone rather than to the α-carbon.

As used herein, the term "physiological conditions" refers to the range of conditions of temperature, pH and tonicity (or osmolality) normally encountered within tissues in the body of a living human.

As used herein, the term "saccharide" refers to the class of carbohydrates including "monosaccharides", "disaccharides" (i.e., two connected monosaccharide units), "oligosaccharides" (i.e., about 3-20 connected monosaccharide units), "polysaccharides" (i.e., over about 20 connected monosaccharide units), and "glycomimetics". Embodiments described herein as referring to "saccharides" may apply to any or all of mono-, di-, oligo-, and polysaccharides, and glycomimetics, all in their D and L stereoisomers, unless indicated otherwise. Monosaccharides include, but are not limited to, Glucose (Glc), Galactose (Gal), Mannose (Man), Talose (Tal), Glucosamine (GlcN), N-acetyl Glucosamine (GlcNAc), D-galactosamine (GalNH$_2$), Glucuronic acid (GlcA), Iduronic acid (IdoA), Galactosamine (GalN), N-acetyl Galactosamine (GalNAc), Fucose (Fuc), Fructose (Fru), Arabinose (Ara), Xylose (Xyl), Rhamnose (Rha), Ribose (Rib), Sialic acid (Neu5Ac), and the like.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence "having at least Y % sequence identity with SEQ ID NO:Z" may have up to X substitutions relative to SEQ ID NO:Z, and may therefore also be expressed as "having X or fewer substitutions relative to SEQ ID NO:Z."

As used herein, the term "structural peptide" refers to a portion of a peptide amphiphile, typically disposed between the hydrophobic segment and the charged peptide segment. The structural peptide is generally composed of three to ten amino acid residues with non-polar, uncharged side chains (e.g., His (H), Val (V), Ile (I), Leu (L), Ala (A), Phe (F)) selected for their propensity to form hydrogen bonds or other stabilizing interactions (e.g., hydrophobic interactions, van der Waals' interactions, etc.) with structural segments of adjacent structural segments. In some embodiments, nanofibers of peptide amphiphiles having structural peptide segments display linear or 2D structure when examined by microscopy and/or α-helix and/or β-sheet character when examined by circular dichroism (CD).

As used herein, the term "sulfated polysaccharide" refers to a class of complex polysaccharides having repeating units of mono- and disaccharides produced by sulfation. Sulfation is a biotransformation involving an enzyme (e.g. a sulfotransferase) catalyzing the transfer of a sulfo group from a donor to the polysaccharide, resulting in a sulfate or sulfamate. Non-limiting examples of sulfated polysaccharides include fucoidans, carrageenans, ulvans, dextran sulfate, and derivatives thereof.

As used herein, the term "supramolecular" (e.g., "supramolecular complex," "supramolecular interactions," "supramolecular fiber," "supramolecular polymer," "supramolecular nanostructure" etc.) refers to the non-covalent interactions between molecules (e.g., polymers, macromolecules, etc.) and the multicomponent assemblies, complexes, systems, and/or fibers that form as a result.

DETAILED DESCRIPTION

Provided herein are compositions comprising peptide amphiphiles (PAs) and methods of use thereof. In particular, provided herein are compositions comprising bone morphogenic proteins bound to peptide amphiphiles, and methods of use of the same for the treatment of cancer. In some embodiments, compositions provided herein may be used for treatment of pediatric brain cancers such as pediatric high-grade glioma (HGG).

In some embodiments, provided herein are compositions comprising peptide amphiphiles. The peptide amphiphiles may be glycosylated (GlncPA or GPA, used interchangeably herein). In some embodiments, the peptide amphiphile may be sulfated. In some embodiments, the peptide amphiphile may be glycosylated and sulfated.

In some embodiments, compositions herein comprise peptide amphiphiles. In some embodiments, the peptide amphiphile molecules and compositions of the embodiments described herein are synthesized using preparatory techniques well-known to those skilled in the art, preferably, by standard solid-phase peptide synthesis, with the addition of a fatty acid in place of a standard amino acid at the N-terminus of the peptide, in order to create the hydrophobic segment (e.g. lipophilic segment). Synthesis typically starts from the C-terminus, to which amino acids are sequentially added using either a Rink amide resin (resulting in an —NH$_2$ group at the C-terminus of the peptide after cleavage from the resin), or a Wang resin (resulting in an —OH group at the C-terminus), or variants thereof. Accordingly, embodiments described herein encompasses peptide amphiphiles having a C-terminal moiety that may be selected from the group consisting of —H, —OH, —COOH, —CONH$_2$, and —NH$_2$. In other embodiments, peptide amphiphiles are synthesized by Fmoc synthesis, where a peptide chain is assembled step-wise into the final PA.

In some embodiments, peptide amphiphiles comprise a hydrophobic segment linked to a peptide. In some embodiments, the hydrophobic segment is a non-peptide hydrophobic segment linked to a peptide. In other embodiments, the peptide segment is a peptide hydrophobic segment. In some embodiments, the peptide linked to the hydrophobic segment comprises a structural segment (e.g., hydrogen-bond-forming segment, beta-sheet-forming segment, etc.), and a charged peptide segment (e.g., acidic segment, basic segment, zwitterionic segment, etc.). In some embodiments, the peptide further comprises linker or spacer segments for adding solubility, flexibility, distance between segments, etc. In some embodiments, peptide amphiphiles comprise a spacer segment (e.g., peptide and/or non-peptide spacer) at the opposite terminus of the peptide from the hydrophobic segment. In some embodiments, the spacer segment comprises peptide and/or non-peptide elements. In some embodiments, the spacer segment comprises one or more functional groups (e.g., alkene, alkyne, azide, thiol, etc.) for the attachment of a mono-, di-, oligo-, or polysaccharide, or glycomimetic residue. In some embodiments, various segments may be connected by linker segments (e.g., peptide (e.g., GG) or non-peptide (e.g., alkyl, OEG, PEG, etc.) linkers).

The lipophilic or hydrophobic segment is typically incorporated at the N-terminus of the peptide amphiphile. In some embodiments, the hydrophobic segment is incorporated at the N-terminus of the peptide amphiphile after the last amino acid coupling, and is composed of a fatty acid or other acid that is linked to the N-terminal amino acid through an acyl bond (although embodiments herein are not limited to such methods). In other embodiments, the hydrophobic segment is a hydrophobic peptide segment. Such a PA, comprising a hydrophobic peptide segment paired to the peptide comprising the charged peptide segment and/or structural peptide segment, may be synthesized by any suitable technique. Exemplary suitable techniques for PA synthesis include, for example, Fmoc solid-phase peptide synthesis.

In aqueous solutions, PA molecules self-assemble (e.g., into cylindrical micelles (nanofibers) that bury the hydrophobic segment (e.g. lipophilic segment) in their core and display the functional peptide and/or saccharide on the surface. The structural peptide undergoes intermolecular hydrogen bonding to form beta sheets that orient parallel to the long axis of the micelle.

In some embodiments, compositions described herein comprise PA building blocks that in turn comprise a hydrophobic segment and a peptide segment. In certain embodiments, a hydrophobic segment (e.g., hydrocarbon and/or alkyl/alkenyl/alkynyl tail, or steroid such as cholesterol) of sufficient length (e.g., 2 carbons, 3 carbons, 4 carbons, 5 carbons, 6 carbons, 7 carbons, 8 carbons, 9 carbons, 10 carbons, 11 carbons, 12 carbons, 13 carbons, 14 carbons, 15 carbons, 16 carbons, 17 carbons, 18 carbons, 19 carbons, 20 carbons, 21 carbons, 22 carbons, 23 carbons, 24 carbons, 25 carbons, 26 carbons, 27 carbons, 28 carbons, 29 carbons, 30 carbons or more, or any ranges there between) is covalently coupled to peptide segment (e.g., a peptide comprising a segment having a preference for beta-strand conformations) to yield a peptide amphiphile molecule. In other embodiments, the hydrophobic segment is a peptide of suitable length (e.g. of a suitable number of amino acids), which may be attached to the peptide segment (e.g. the structural peptide segment or charged peptide segment) to yield peptide amphiphile molecule.

In some embodiments, a plurality of PAs will self-assemble in water (or aqueous solution) into a nanostructure (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces; 2nd ed.; Academic: London San Diego, 1992; herein incorporated by reference in its entirety). Other molecular shapes have similar effects on assembly and nanostructural architecture. In various embodiments, hydrophobic segments pack in the center of the assembly with the peptide/saccharide segments exposed to an aqueous or hydrophilic environment to form cylindrical nanostructures that resemble filaments. Such nanofilaments display the peptide or saccharide regions on their exterior and have a hydrophobic core.

In some embodiments, to induce self-assembly of an aqueous solution of peptide amphiphiles, the pH of the solution may be changed (raised or lowered) or mono-/multivalent ions, such as sodium or calcium, or charged polymers or other macromolecules may be added to the solution.

In some embodiments, the hydrophobic segment is a non-peptide segment (e.g., alkyl/alkenyl/alkynyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, heterocyclic rings, aromatic segments, pi-conjugated segments, cycloalkyls, oligothiophenes etc. In some embodiments, the hydrophobic segment comprises an acyl/ether chain (e.g., saturated) of 2-30 carbons (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30). In other embodiments, the hydrophobic segment is a peptide (e.g. a peptide containing sufficient number of hydrophobic amino acid residues to be hydrophobic in nature). Exemplary hydrophobic segments that are peptides include, for example, Q11 peptide or derivatives thereof. The sequence of the Q11 peptide is QQKFQFQFEQQ (SEQ ID NO: 3).

In some embodiments, PAs comprise one or more peptide segments. The peptide segment may comprise natural amino acids, modified amino acids, desipeptides, peptidomimetics, or combinations thereof. In some embodiments, peptide segment comprise at least 50% sequence identity or similarity (e.g., conservative or semi-conservative) to one or more of the peptide sequences described herein.

In some embodiments, peptide amphiphiles comprise a charged peptide segment. The charged peptide segment may be acidic, basic, or zwitterionic. In some embodiments, the charged peptide segment is chemically functionalized with one more groups selected from sulfates, sulfonates, phosphates, phosphonates, quaternary ammonium, and heterocycles.

In some embodiments, peptide amphiphiles comprise an acidic peptide segment. For example, in some embodiments, the acidic peptide comprises one or more (e.g., 1, 2, 3, 4, 5, 6, 7, or more) acidic residues (D and/or E) in sequence. For example, the charged peptide segment may comprise $E_{2-6}$. For example, the charged peptide segment may comprise EE, EEE, or EEEE. In some embodiments, the acidic peptide segment comprises up to 7 residues in length and comprises at least 50% acidic residues. In some embodiments, an acidic peptide segment comprises $(Xa)_{1-7}$, wherein each Xa is independently D or E. In some embodiments, an acidic peptide segment comprises EE.

In some embodiments, peptide amphiphiles comprise a basic peptide segment. For example, in some embodiments, the acidic peptide comprises one or more (e.g., 1, 2, 3, 4, 5, 6, 7, or more) basic residues (R, H, and/or K) in sequence. In some embodiments, the basic peptide segment comprises up to 7 residues in length and comprises at least 50% basic residues. In some embodiments, an acidic peptide segment comprises $(Xb)_{1-7}$, wherein each Xb is independently R, H, and/or K.

In some embodiments, peptide amphiphiles comprises a structural and/or beta-sheet-forming segment. In some embodiments, the structural segment is rich in H, I, L, F, V, and A residues. In some embodiments, the structural and/or beta-sheet-forming segment comprises an alanine- and valine-rich peptide segment (e.g., AAVV (SEQ ID NO: 1), AAAVVV (SEQ ID NO: 2), or other combinations of V and A residues, etc.). In some embodiments, the structural and/or beta sheet peptide comprises 4 or more consecutive A and/or V residues, or conservative or semi-conservative substitutions thereto. In some embodiments, the structural and/or beta-sheet forming peptide segment comprises 4 or more consecutive non-polar aliphatic residues (e.g., alanine (A), valine (V), leucine (L), isoleucine (I), methionine (M)). In some embodiments, the structural and/or beta-sheet forming peptide segment comprises 2-16 amino acids in length and comprises 4 or more (e.g., 2, 3, 4, 5, 6, 7, 8, 9, 10, 11, 12, 13, 14, 15, 16, or ranges there between) non-polar aliphatic residues.

In some embodiments, peptide amphiphiles comprise a non-peptide spacer or linker segment. In some embodiments, the non-peptide spacer or linker segment is located at the opposite terminus of the peptide from the hydrophobic segment. In some embodiments, the spacer or linker segment provides the attachment site for a functional group. In some embodiments, the spacer or linker segment provides a reactive group (e.g., alkene, alkyne, azide, thiol, maleimide etc.) for functionalization (e.g., glycosylation) of the PA. In some embodiments, the spacer or linker is a substantially linear chain of CH2, O, $(CH_2)_2O$, $O(CH_2)_2$, NH, and C=O groups (e.g., $CH2(O(CH_2)_2)_2NH$, $CH2(O(CH_2)_2)_2NHCO(CH_2)_2CCH$, etc.). In some embodiments, a spacer or linker further comprises additional functional groups, substituents, branches, etc.

Suitable peptide amphiphiles, PA segments, PA nanostructures, and associated reagents and methods are described, for example in U.S. Pat. Nos. 8,512,693; 8,450,271; 8,138,140; 8,124,583; 8,114,835; 8,114,834; 8,080,262; 8,063,014; 7,851,445; 7,838,491; 7,745,708; 7,683,025; 7,554,021; 7,544,661; 7,534,761; 7,491,690; 7,452,679; 7,390,526; 7,371,719; 6,890,654; and U.S. Pat. Pub. No. 20180125924A1; herein incorporated by reference in their entireties.

The characteristics (e.g., shape, rigidity, hydrophilicity, etc.) of a PA supramolecular structure depend upon the identity of the components of a peptide amphiphile (e.g., hydrophobic segment, acidic segment, structural segment, functional segment, etc.). For example, nanofibers, nanospheres, intermediate shapes, and other supramolecular structures are achieved by adjusting the identity of the PA component parts. In some embodiments, characteristics of supramolecular nanostructures of PAs are altered by post-assembly manipulation (e.g., heating/cooling, stretching, etc.).

In some embodiments, a peptide amphiphile comprises: (a) a hydrophobic segment; (b) a structural segment (e.g., comprising VVAA); and (c) a charged peptide segment (e.g., comprising EE, EEE, or EEEE). In some embodiments, the peptide amphiphile further comprises an attachment segment (e.g., K) for attachment of a functional group (e.g., attachment of a spacer, glycosylation, etc.).

In some embodiments, provided herein compositions comprising glycosylated peptide amphiphiles and self-assembled nanostructures (e.g., nanofibers) thereof. Glycosylated PAs display a mono, di-, oligo-, or polysaccharide, or glycomimetic at one terminus (e.g., opposite terminus as the hydrophobic segment).

In some embodiments, the saccharide is a mono, di-, oligosaccharide, or glycomimetic that mimics the function of a particular polysaccharide in a biological context (e.g., protein binding (e.g., to the heparin binding site of growth factors, etc.), etc.). In some embodiments, the saccharide is a mono, di-, oligosaccharide that mimics a glycosaminoglycan.

In some embodiments, glycosylated peptide amphiphiles are provided displaying a monosaccharide (e.g., at the terminus opposite the hydrophobic segment). Suitable monosaccharides include 1,2-cis/1,2-trans glycosides (alfa/beta anomers) from pentoses, hexoses, hexosamines, heptoses, heptosamines, octoses, and nonoses in the form of pyranoses and furanoses in both L- and D-form. Exemplary monosaccharides for conjugation to PAs and nanostructures herein include, but are not limited to: (i) hexoses such as galactose, glucose, mannose, talose, (ii) hexosamines such as galactosamine, glucosamine, mannosamine, talosamine; (iii) hexosamine derivatives such as N-acetylation of galactosamine, glucosamine, mannosamine, talosamine, (iv) ulosonic- and uronic acids such as KDO (3-Deoxy-D-manno-oct-2-ulosonic acid), glucuronic acid and iduronic acids, (v) sialic acids such as neuraminic acid, N-acetylneuraminic acid and N-glycolylneuraminic acid; (vi) deoxy sugars such as rhamnose, fucose; (vii) pentoses such as arabinose, ribose, and xylose; (viii) heptoses such as L-glycero-D- mannoheptulose. Other suitable classes of glycomimetics for conjugation to the PAs herein include, but are not limited to: (i) aza-sugars, (ii) c-glycosides, (iii) carbasugars, (iv) thiosugars, (v) sulfosugars, (vi) thioglycosides, (vii) iminosugars, (viii) phospha sugars, (ix) glycosylamines, (x) lactones, (xi) pseudo-sugars, (xii) aminocyclitols, (xiii) cyclitols, (xiv) polyols, (xv) inositols such as myo-inositol and scyllo-inositols.

In some embodiments, the monosaccharides are functionalized to include one or more additional or alternative functional groups. For example, exemplary functionalizations of the monosaccharides and possible salts thereof include, but not limited to: (i) amino groups, (ii) acetamides, (iii) carboxymethylates, (iv) phosphates, (v) phosphonates, (vi) 0-/N-sulfates, (vii) sulfonates, (viii) bioisosteres and (vii) radiolabeling, for example with 18F or para-magnetic with 19F. Suitable bioisoteres include, for example, hydrogen and fluoride, deuterium and hydrogens, carboxylic acid and the tetrazole ring, carboxylic acid and acyl sulfonamide, carboxylic acid and aryl sulfonamide, amide and imidazole, amide and ester, amide and carbamate, amide and urea, etc.

In some embodiments, PAs are conjugated with di-, oligo, or polysaccharides, or glycomimetics. The aforementioned monosaccharides may be combined in any suitable combinations to yield di-, oligo-, or polysaccharides with different structures, different degrees of sulfation, bioactivities, and applications. Exemplary di-, oligo-, or polysaccharides, or glycomimetics include, but not limited to: (i) disaccharides such as Hyaluronic acid disaccharides (e.g., D-glucuronic acid and D-N-acetylglucosamine), heparin-/heparan sulfate disaccharides (e.g., GlcA-GlcNAc, GlcA-GlcNS, IdoA-GlcNS, IdoA(2S)-GlcNS, IdoA-GlcNS(6S), IdoA(2S)-GlcNS(6S), etc.), cellobiose, maltose, lactulose, chitobiose, N,N'-diacetylchitobiose, lactose, lactosamine, N-acetyl lactosamine, maltose, sucrose, trehalose, cellobiose, mannobiose; (ii) oligosaccharides such as Sialyl Lewis$^x$, glycosylphosphatidylinositol (GPI-anchors), GAG-oligosaccharides, globotriose, sulfated GAG-oligosaccharides, fucoidan oligosaccharides, and sulfated fucoidan oligosaccharides; (iii) glycomimetics such as kanamycin, neomycin, streptomycin. In some embodiments, oligosaccharides or polysaccharides of Hyaluronic acid disaccharides (e.g., D-glucuronic acid and D-N-acetylglucosamine), heparin-/heparan sulfate disaccharides (e.g., GlcA-GlcNAc, GlcA-GlcNS, IdoA-GlcNS, IdoA(2S)-GlcNS, IdoA-GlcNS(6S), IdoA(2S)-GlcNS(6S), etc.) are provided.

In some embodiments, the di-, oligo-, or polysaccharides are functionalized to include one or more additional or alternative functional groups. For example, exemplary functionalizations of the monosaccharides and possible salts thereof include, but not limited to: (i) amino groups, (ii) acetamides, (iii) carboxymethylates, (iv) phosphates, (v) phosphonates, (vi) 0-/N-sulfates, (vii) sulfonates, (viii) bioisosteres and (vii) radiolabeling, for example with 18F or para-magnetic with 19F. Suitable bioisoteres include, for example, hydrogen and fluoride, deuterium and hydrogens, carboxylic acid and the tetrazole ring, carboxylic acid and acyl sulfonamide, carboxylic acid and aryl sulfonamide, amide and imidazole, amide and ester, amide and carbamate, amide and urea, etc.

In some embodiments, in addition to the core saccharide structure, the saccharides for conjugation to a PA further comprise a linker, attachment moiety, or reactive functional group. In some embodiments, the saccharide is attached to a spacer or linker segment on the peptide amphiphile. In some embodiments, the spacer or linker segment displays a functional group that will react to form a covalent bond with a functional group on the saccharide (or a compound comprising the saccharide (and a linker)). Linkers and suitable reaction chemistries are described herein. Exemplary pairs of functional groups for attaching the saccharide to the PA are alkyne/azide, thiol/maleimide, thiol/haloacetyl (e.g., iodoacetyl, etc.), azide/phosphine (Staudinger ligation), thiol/pyridyl disulfide (e.g. pyridyldithiol, etc.), sulphonyl azides/thio acids, transcyclooctene and tetrazine groups, dibenzocyclooctyne and azide groups, etc. In some embodiments, the saccharide (or compound comprising the saccharide) and the PA each display one of a reactive pair of functional groups capable of undergoing a Huisgen cycloaddition or alkene hydrothiolation.

In some embodiments, an appropriate saccharide, in terms of both identity and length, is selected for a particular target and/or application. Exemplary targets/applications of glycosylated PAs and supramolecular glyconanostructures include the use of glycosylated PAs conjugated to growth factors, such as BMP4, for use in cancer treatment methods.

In some embodiments, provided herein are glycosylated peptide amphiphiles comprising any combination of peptide amphiphile elements (e.g., the hydrophobic segments, structural segments, charged peptide segments, linkers, spacers, and functional groups described herein, incorporated by reference, or understood in the field), saccharides, linkers, and connection chemistries (e.g., alkyne/azide, etc.).

In some embodiments, the GPA is a GAG mimetic PA. A GAG mimetic PA is a peptide amphiphile that is conjugated to a mono-, di-, oligo-, or polysaccharide, or glycomimetic and is capable of exerting a bioactivity (e.g., binding to a bone morphogenic protein) of a glycosaminoglycan (e.g., hyaluronic acid, heparin, heparan sulfate, etc.) in a relevant context (e.g., in vitro, in vivo, in a subject (e.g., at the site of a brain tumor), etc.). In some embodiments, a GAG mimetic displays a saccharide (e.g., monosaccharide, disaccharide, oligosaccharide, etc.) that is found in natural GAGs (e.g., monosaccharides such as GlcA, GlcNAc, GlcNS, IdoA, IdoA(2S), GlcNS(6S), GlcNAc(3,4,6S), etc., and disaccharides/oligosaccharides combining such monosaccharides).

In some embodiments, GPAs, like the PAs they comprise and/or are formed from, self-assemble (e.g., in aqueous conditions, under known conditions, etc.) into supramolecular nanostructures (e.g., nanofibers) referred to herein as supramolecular glyconanostructures (or, for example, supramolecular glyconanofibers). The term "glyconanostructure" is used herein to describe a type of nanostructure containing at least one GPA. In some embodiments, supramolecular glyconanostructures comprise a hydrophobic core and structured (e.g., supported by hydrogen bonding and/or beta-sheet structure) and charged peptide exterior, and display glycosylated features on the exterior. In some embodiments, the glycosylated terminus of the PAs are displayed on the exterior of the nanostructures. In some embodiments, the glycosylated terminus of the PAs are bound to a protein, such a bone morphogenic protein (e.g. BMP-4), which is thereby displayed on the exterior of the nanostructure.

In some embodiments, glyconanostructures are assembled from GPAs and filler peptide amphiphiles (e.g., non-glycosylated PAs). In some embodiments, nanostructures (e.g., nanofibers) comprise: (i) less than 50% (e.g., 49%, 45%, 40%, 35%, 30%, 25%, 20%, 15%, 10%, 5%, 4%, 3%, 2%, 1%, or any ranges there between) GPAs; and/or (ii)

less than 50% (e.g., 49%, 45%, 40%, 35%, 30%, 25%, 20%, 15%, 10%, 5%, 4%, 3%, 2%, 1%, or any ranges there between) filler peptide amphiphiles. Some embodiments, glyconanostructures (e.g., nanofibers) comprise and at least 2% (e.g., 2%, 3%, 4%, 5%, 10%, 15%, 20%, 25%, 30%, 35%, 40%, 45%, 50%, 55%, 60%, 65%, 70%, 75%, 80%, 85%, 90%, 95%, 98%, or any ranges there between) filler peptide amphiphiles. In some embodiments, nanofibers comprise at least 50% (e.g., 50%, 55%, 60%, 65%, 70%, 75%, 80%, 85%, 90%, 95%, 98%, or any ranges there between) filler peptide amphiphiles. In some embodiments, the ratio of GPAs to filler PAs determines the density of saccharides displayed on the nanostructure surface.

In some embodiments, supramolecular glyconanostructures are assembled from PAs comprising (e.g., in addition to filler PAs) GAG mimetic PAs. Such supramolecular glyconanostructures are referred to herein as "supramolecular GAG mimetics" or "supramolecular GAG mimetic nanostructures." In some embodiments, supramolecular GAG mimetics comprise a hydrophobic core and structured (e.g., supported by hydrogen bonding and/or beta-sheet structure) and charged peptide exterior, and display saccharides on their exterior that are capable of mimicking one or more bioactivities of a GAG (e.g., binding to a heparin binding domain of growth factors such as BMP4, etc.).

In some embodiments, PAs are provided that have a high binding affinity for a protein of interest (e.g., a bone morphogenic protein such as BMP-4). In some embodiments, glycosylated PAs (e.g., supramolecular GAG mimetics) are provided that have a high binding affinity for a protein of interest (e.g., a bone morphogenic protein) and/or a specific binding domain of the protein of interest (e.g., the heparin-binding domain). In some embodiments, glycosylated PAs (e.g., supramolecular GAG mimetics) are provided having binding affinity for the heparin binding domain of a bone morphogenic protein (e.g., BMP-2, BMP-4). In some embodiments, non-glycosylated PAs (e.g. E2-PAs) are provided having a binding affinity for a bone morphogenic protein. For example, glycosylated PAs and/or non-glycosylated PAs may have a binding affinity for BMP-4. The binding affinity ($K_d$) may be chosen from one of: less than 10 μM, less than 1 μM, less than 100 nM, less than 10 nM, less than 1 nM, less than 100 μM.

structure, and the bone morphogenic protein binds to the surface of the glyconanostructure.

In some embodiments, the bone morphogenic protein binds to the glycosylated PA. For example, the glycosylated PA may comprise a bound bone morphogenic protein. As another example, the bone morphogenic protein may bind to a non-glycosylated PA, such as an E2-PA. for example, the E2-PA may comprise a bound bone morphogenic protein. The bone morphogenic protein may be BMP2, BMP3 (e.g. BMP3B) BMP4, BMP5, BMP6, BMP7, BMP8 (e.g. BMP8a, BMP8b) BMP9, BMP10, BMP11, BMP12, or BMP15. For example, the E2-PAs and/or glycosylated PAs may comprise BMP-4. In some embodiments, the bone morphogenic protein (e.g. BMP-4) binds to the charged peptide segment of a PA (e.g. of a non-glycosylated PA, such as an E2-PA). In some embodiments, the bone morphogenic protein binds to the PA through electrostatic charge, where the negative charge units on the PA (e.g. the charged peptide segment of the non-glycosylated PA) have an affinity for the positive regions on the bone morphogenic protein (e.g. BMP-4).

In some embodiments, the bone morphogenic protein (e.g. BMP-4) binds to an E2-PA. The bone morphogenic protein, such as BMP-4, may bind to the E2-PA via electrostatic charge, where the negative charge units on the E2-PA (e.g. glutamic acids of the E2 PA) have an affinity for the positive regions on the bone morphogenic protein (e.g. BMP-4).

In some embodiments, the bone morphogenic protein (e.g. BMP-4) binds to the saccharide of the glycosylated PA. For example, the bone morphogenic protein (e.g. BMP-4) may bind to a sulfated saccharide on the glycosylated PA. In particular embodiments, the bone morphogenic protein (e.g. BMP-4) binds to a tri-sulfated monosaccharide on the glycosylated PA. In some embodiments, the bone morphogenic protein binds to the glycosylated PA through electrostatic charge, where the negative charge units on the glycosylated PA (e.g. the saccharide unit of the glycosylated PA) have an affinity for the positive regions on the bone morphogenic protein (e.g. BMP-4).

An exemplary glycosylated peptide amphiphile is shown below:

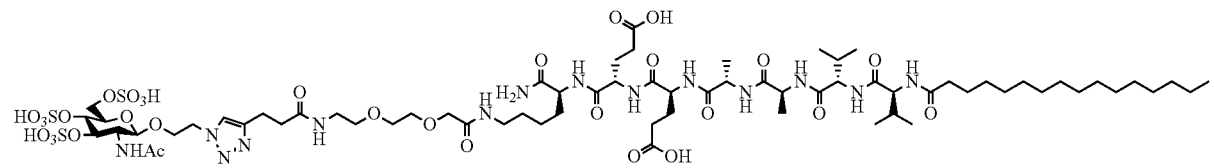

In some embodiments, the compositions provided herein comprise a protein of interest. In some embodiments, the compositions comprise a bone morphogenic protein. In some embodiments, the compositions comprise a plurality of GPAs and a bone morphogenic protein. The plurality of GPAs are configured to form a self-assembled glyconano- The tri-sulfated glycosylated peptide amphiphile shown above may be bound to a bone morphogenic protein, such as BMP-4, via electrostatic interactions of the positive charged region of BMP4 with the negatively charged saccharide unit on the glycosylated PA.

An exemplary non-glycosylated peptide amphiphile, referred to herein as E2-PA, is shown below:

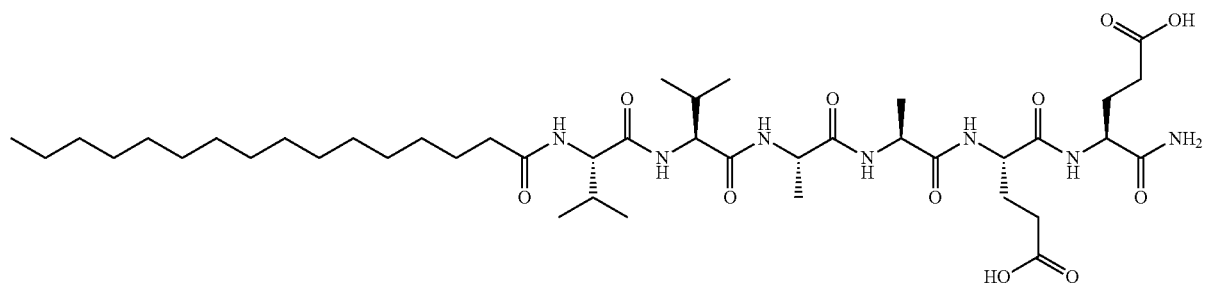 [SMILES: CCCCCCCCCCCCCCCC(=O)N[C@H](C(=O)N[C@H](C(=O)N[C@@H](C)C(=O)N[C@@H](C)C(=O)N[C@@H](CCC(=O)O)C(=O)N[C@@H](CCC(=O)O)C(N)=O)C(C)C)C(C)C]

In some embodiments, the compositions described herein are used for the treatment of cancer. In some embodiments, compositions comprising glycosylated PAs (e.g., supramolecular GAG mimetics, etc.) and/or non-glycosylated PAs (e.g. E2-PAs) described herein and nanostructures self-assembled therefrom are used in the treatment of cancer. For example, the composition comprising a plurality of glycosylated PAs and/or non-glycosylated PAs and a bone morphogenic protein, such as BMP-4, or a nanostructure self-assembled therefrom may be used in the treatment of cancer. The cancer may be in an adult or a pediatric subject. For example, a composition comprising a plurality of glycosylated PAs configured to form a glyconanostructure and a bone morphogenic protein, such as BMP-4, that binds to the surface of the glyconanostructure may be used for the treatment of a cancer. As another example, a composition comprising a plurality of PAs (e.g. non-glycosylated PAs) configured to self-assemble into a nanostructure and a bone morphogenic protein, such as BMP-4, that binds to the surface of the nanostructure may be used for the treatment of a cancer.

In some embodiments, the cancer is selected from adenoid cystic carcinoma, adrenal gland cancer, amyloidosis, anal cancer, basal cell carcinoma, bile duct cancer, bladder cancer, bone cancer, brain cancer, breast cancer, carcinoid tumor, cervical cancer, colorectal cancer, ductal carcinoma, endometrial cancer, esophageal cancer, gastric cancer, gastrointestinal stromal tumor, islet cell tumor, kidney cancer, laryngeal cancer, leukemia, liver cancer, lobular carcinoma, lung cancer (e.g. small cell lymphoma, non-small cell lung cancer, Hodgkin's Lymphoma, Non-Hodgkin's lymphoma), malignant glioma, melanoma, meningioma, multiple myeloma, myelodysplastic syndrome, nasopharyngeal cancer, neuroendocrine tumor, oral cancer, osteosarcoma, ovarian cancer, pancreatic cancer, pancreatic neuroendocrine tumors, parathyroid cancer, penile cancer, peritoneal cancer, pituitary gland tumor, prostate cancer, renal cell carcinoma, retinoblastoma, salivary gland cancer, sarcoma, skin cancer, small intestine cancer, stomach cancer, testicular cancer, thyoma, thyroid cancer, uterine cancer, endometrial cancer, and vaginal cancer.

In some embodiments, the cancer is a brain cancer. Suitable brain cancers include, for example, gliomas (e.g. astrocytomas, ependymomas, glioblasmota multiforme, medulloblastomas, high-grade gliomas, oligodendrogliomas), hemangioblastomas, and rhabdoid tumors. In some embodiments, the glycosylated PAs and/or non-glycosylated PAs provided herein may be bound to a bone morphogenic protein (e.g. BMP-4) for use in the treatment of a brain cancer in an adult subject. In some embodiments, the glycosylated PAs and/or non-glycosylated PAs provided herein may be bound to a bone morphogenic protein (e.g. BMP-4) for use in the treatment of brain cancer in a pediatric subject. In some embodiments, the brain cancer in a pediatric subject is a pediatric high grade glioma.

In some embodiments, a composition comprising glycosylated PAs (e.g., GAG mimetic PA, etc.), non-glycosylated PAs (e.g. E2-PAs) or nanostructures self-assembled therefrom is provided, optionally in combination with a pharmaceutically acceptable carrier, adjuvant or diluent. In some embodiments, the composition further comprises other agents useful in cancer medicine. For example, in some embodiments, the composition further comprises a chemotherapeutic agent. Suitable chemotherapeutic agents include, for example, alkylating agents, nitrosoureas, antimetabolites, topoisomerase inhibitors, anti-tumor antibiotics, mitotic inhibitors, and corticosteroids. In some embodiments, the chemotherapeutic agent is an alkylating agent, such as Altretamine, Bendamustine, Busulfan, Carmustine, Chlorambucil, Cyclophosphamide, Dacarbazine, Ifosfamide, Lomustine, Mechlorethamine, Melphalan, Temozolomide, Thiotepa, or Trabectedin. In some embodiments, the chemotherapeutic agent is an "alkylating-like", platinum-based antineoplastic agent. Examples of alkylating-like agents include Cisplatin, Carboplatin, Dicycloplatin, Eptaplatin, Lobaplatin, Miriplatin, Nedaplatin, Oxaliplatin, Picoplatin, Satraplatin, and Triplatin tetranitrate.

some embodiments, the chemotherapeutic agent is cisplatin. In some embodiments, the chemotherapeutic agent is carboplatin. In some embodiments, a chemotherapeutic agent is administered to the subject in conjunction with a composition described herein. For example, a chemotherapeutic agent such selected from alkylating agents, nitrosoureas, antimetabolites, topoisomerase inhibitors, anti-tumor antibiotics, mitotic inhibitors, and corticosteroids may be administered to the subject in conjunction with a composition described herein. The chemotherapeutic agent and the composition may be administered simultaneously or sequentially. The order of administration and the spacing between administration may be selected depending on the subject and the needs thereof. In some embodiments, the chemotherapeutic agent is administered to the subject after the composition comprising the bone morphogenic protein. For example, the subject may be administered the composition comprising the bone morphogenic protein and, at a suitable time point after, may be administered the chemotherapeutic agent. For example, the chemotherapeutic agent may be provided to the subject 1 minute, 10 minutes, 30 minutes, 1 hour, 2 hours, 3 hours, 4 hours, 5 hours, 6 hours, 7 hours, 8 hours, 9 hours, 10 hours, 12 hours, 24 hours, 2 days, 3 days, 4 days, 5 days, 6 days, 7 days, 8 days, 9 days, 10 days, 2 weeks, 3 weeks, 1 month, or more than 1 month after the composition comprising the bone morphogenic protein. In other embodiments, the composition comprising the bone morphogenic protein and the chemotherapeutic agent may be provided to the subject simultaneously. The composition and/or chemotherapy may be provided to the subject repeatedly (e.g. more than one dose may be given) at varying time points. In other embodiments, the composition and/or chemotherapy may be provided to the subject once.

In some embodiments, a composition comprising a bone morphogenic protein bound to a PA, such as a GPA or E2-PA, improves one or more functions of the bone morphogenic protein compared to the bone morphogenic protein in an unbound state (e.g. not incorporated into a glyconanostructure comprising the PA). Accordingly, the compositions described herein may permit combination therapy with a chemotherapeutic agent, as described above, while enabling a smaller effective therapeutic dose of the chemotherapeutic agent to be used. In other words, the compositions described herein may render cells more susceptible to chemotherapy. Accordingly, undesirable side effects associated with the chemotherapeutic agent can be reduced or eliminated by using the agent in combination with the composition comprising a BMP bound to a PA, as described herein.

Pharmaceutical compositions are provided for use in, for example, the treatment of cancer (e.g. brain cancer) in an adult or pediatric subject. The use of glycosylated PAs (e.g., supramolecular GAG mimetics, etc.) and/or non-glycosylated PAs in the manufacture of a medicament for the treatment of cancer (e.g. brain cancer) is also provided. In some embodiments, a pharmaceutical composition comprises supramolecular assemblies (e.g., nanoparticles, nanofibers, etc.) of glycosylated PAs (e.g., GAG mimetic PAs) bound to a bone morphogenic protein, such as BMP-4. In some embodiments, a composition comprises supramolecular assemblies of non-glycosylated PAs (e.g. E2-PAs) bound to a bone morphogenic protein, such as BMP-4. In some embodiments, a composition comprises glycosylated PAs and non-glycosylated PAs, wherein one or each type of PA is bound to a bone morphogenic protein (e.g. BMP-4). In some embodiments, the pharmaceutical composition further comprises additional therapeutic agents, such as additional therapeutic agents for the treatment of cancer, such as antibodies, chemotherapeutic agents, and the like. In some embodiments, the pharmaceutical composition is administered locally to a treatment site (e.g., delivered intracranially to/near the location of a tumor). In some embodiments, the pharmaceutical composition is administered systemically.

In some embodiments, the PAs (e.g., glycosylated PAs, non-glycosylated PAs, etc.) described herein and/or nanostructures self-assembled therefrom are useful in a range of applications, in vitro and/or in vivo, for example, treatment of cancer either in cell or tissue culture in vitro, or in cells or tissue in vivo.

In some embodiments, a method of treating a brain cancer a subject in need of such treatment is provided, the method comprising administering an effective amount of or nanostructures self-assembled therefrom to the subject. The administered supramolecular nanostructures (e.g., supramolecular GAG mimetics) may be formulated in a suitable pharmaceutical composition or medicament and may further comprise a pharmaceutically acceptable carrier, adjuvant or diluent. The composition may be delivered to the subject in combination with other suitable therapies for the treatment of cancer. For example, the composition may be delivered in combination with other suitable cancer therapies, including surgery, chemotherapy, radiation therapy, transplant, immunotherapy, hormone therapy, targeted drug therapy, cryoablation, radiofrequency ablation, or other suitable therapeutic methods. The composition may be provided prior to, concurrently with, or after other suitable therapies are provided to the subject. The composition may be provided to the subject once or multiple times. For example, the composition may be provided to the subject at multiple time points over a suitable time window.

EXPERIMENTAL

Example 1

Pediatric high-grade glioma (HGG) is among the most formidable cancer occurring in childhood. Gross total surgical resection with subsequent chemo- and radiation therapy has proven non-curative in nearly all instances. Results indicate that the level of histone H3 lysine 4 trimethylation (H3K4me3) is directly correlated with tumor malignancy as well as prognosis for pediatric patients with HGG, which suggests that reducing tumor H3K4me3 could be an effective treatment strategy for HGG.

Bone morphogenetic protein 4 (BMP4) induces apoptosis and in so doing also increases cell sensitivity to cytotoxic therapies. Higher levels of intratumoral BMP4 have been associated with a more favorable prognosis, consistent with the concept that treating tumors with exogenous BMP4 could prove effective in various types of cancer. The mechanisms by which BMP4 increases tumor cell sensitivity to cytotoxic and radiation therapies are poorly understood. Recent studies have shown that BMP4 influences DNA methylation that, in turn, influences gene expression. Little is known about BMP4 effects on another type of epigenetic gene regulation: posttranslational histone modifications (PTMs).

In this example, gene expression and histone modification alterations following BMP4 treatment are evaluated to help determine how BMP4-associated histone modifications influence HGG sensitivity to cytotoxic therapies. In vitro studies are performed to compare BMP4-bearing glycopeptide nanostructures vs. free BMP4 for anti-tumor activity. In vivo studies for evaluating the efficacy of BMP4 nanostructures in treating orthotopic HGG xenograft models are demonstrated herein. Such studies elucidate the molecular basis for BMP4 increasing tumor cell sensitivity to cytotoxic/genotoxic therapies; and the extent to which BMP4-bearing nanofibers extend BMP4 activity.

The present disclosure investigates novel sulfated glycopeptide nanostructures carrying BMP4 as a delivery platform for extending therapeutic activity both in vitro and in vivo. Additional innovative aspects include determining the effects of BMP4 on histone PTMs, and relationships between PTMs and DNA repair gene expression, and investigation of interactions between BMP4 and cytotoxic therapy treatments.

The disclosure investigates tumor cell histone PTM and gene expression responses to BMP4, and investigates these responses with respect to pediatric glioma cell sensitivity to cytotoxic/genotoxic therapies. In doing so, the clinical potential of a BMP4 peptide nanostructure platform for treating HGGs is demonstrated.

Figure 1C:
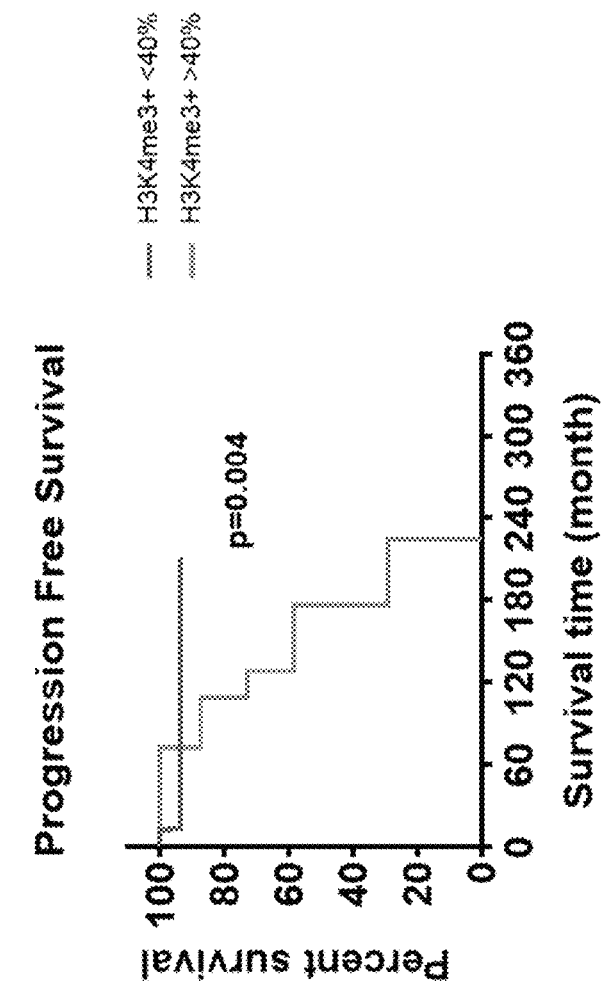
Figure 1B:
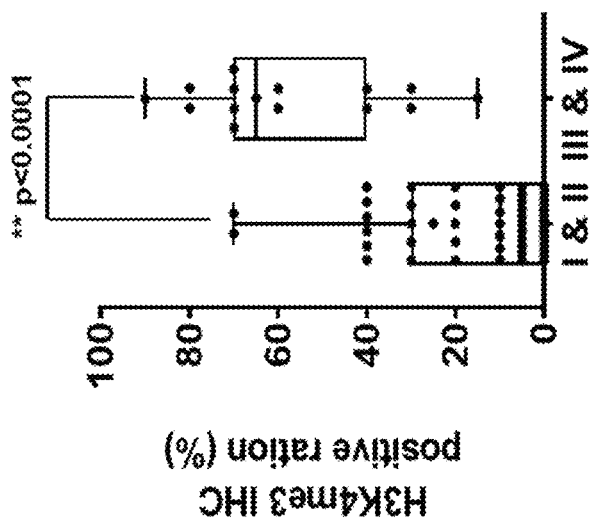

H3K4me3 levels and H3K4 PTM modifier expression correlate with glioma malignancy and prognosis. Recent studies have shown the levels and types of histone H3 PTMs are distinct in brain tumors, in relation to normal brain. Results indicate that H3K4me3 levels in pediatric gliomas are directly correlated with tumor malignancy and patient prognosis (FIG. 1A-C). These observations suggest that reducing tumor H3K4me3 may be an effective strategy for treating HGG.

Figure 1D:
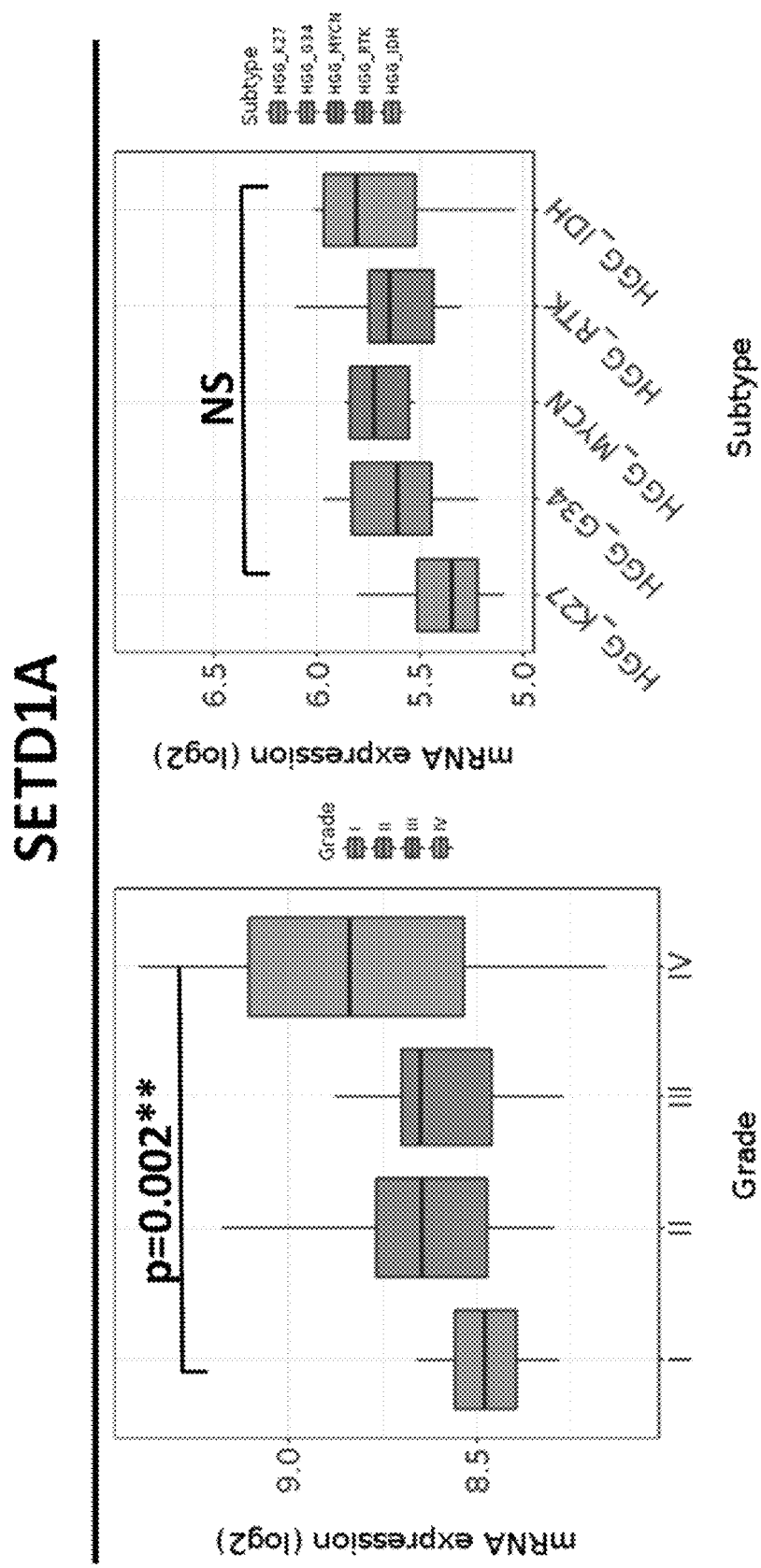
Figures 1E, 1F:
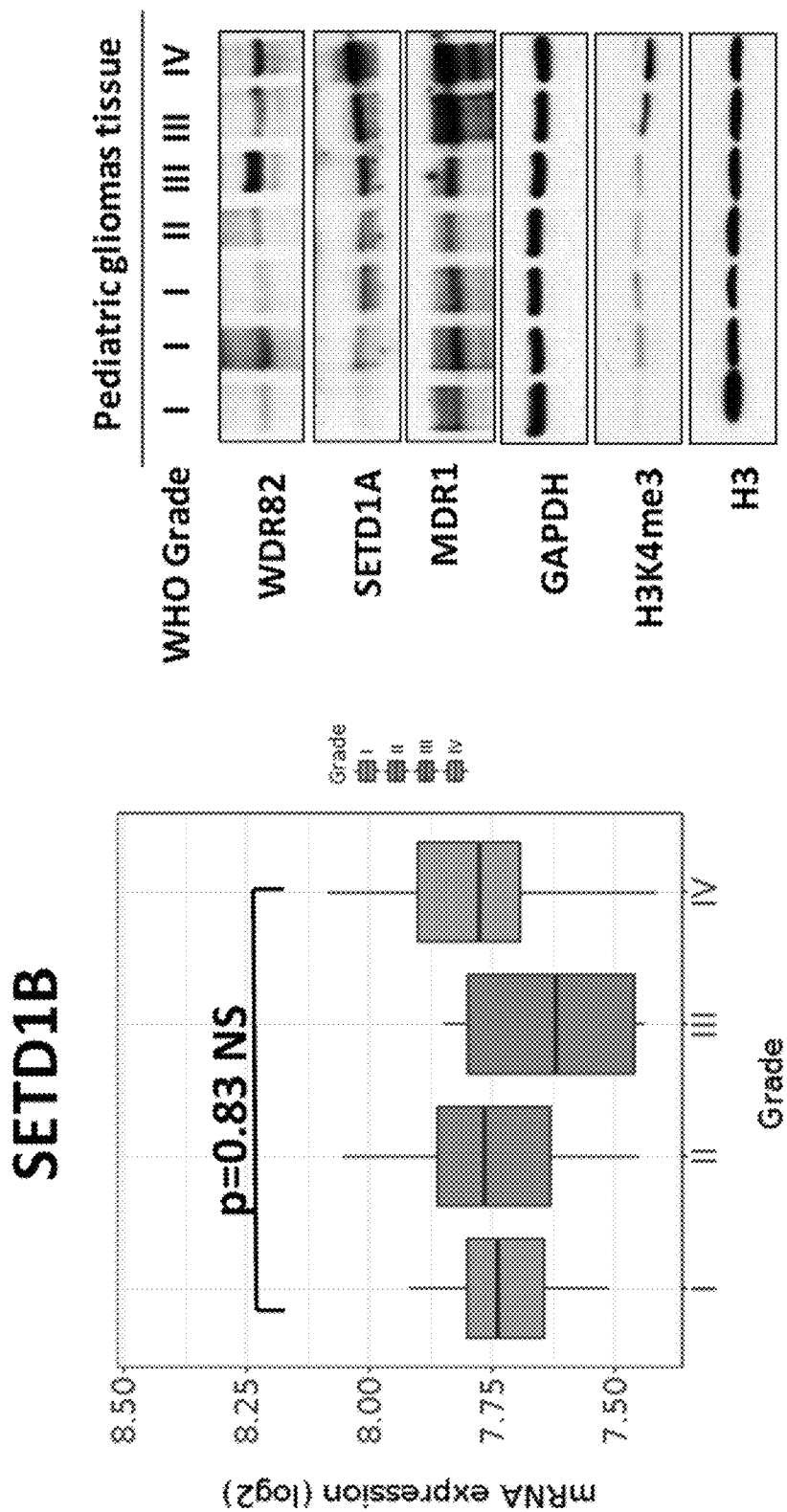

There are two direct approaches for reducing global H3K4me3: enhancing the activity of H3K4 demethylases or inhibiting H3K4 methyltransferases. To identify demethylase and methyltransferase levels in pediatric gliomas, expression was analyzed in the GEO dataset (GSE50161) using the Gliovis online platform (http://gliovis.bioinfo.cnio.es/). Expression levels in pediatric glioma tumor specimens from surgical cases at Lurie Children's Hospital of Chicago (IRB #2005-12252) were also analyzed. Results of both types show that SETD1A methyltransferase expression associates with WHO malignancy grade, and is not dependent on the presence or absence of histone H3 mutations (FIGS. 1D and F). This relationship was not evident for SETD1B (FIG. 1E), which is structurally similar to SETD1A. Interestingly, numerous studies have shown that SETD1A is essential for pluripotency of multiple stem cell types including neural stem cells. The role of SETID1A in HGG has yet to be investigated. Results in FIG. 1 suggest that SETD1A activity is an important determinant of HGG malignancy.

Figure 2A:
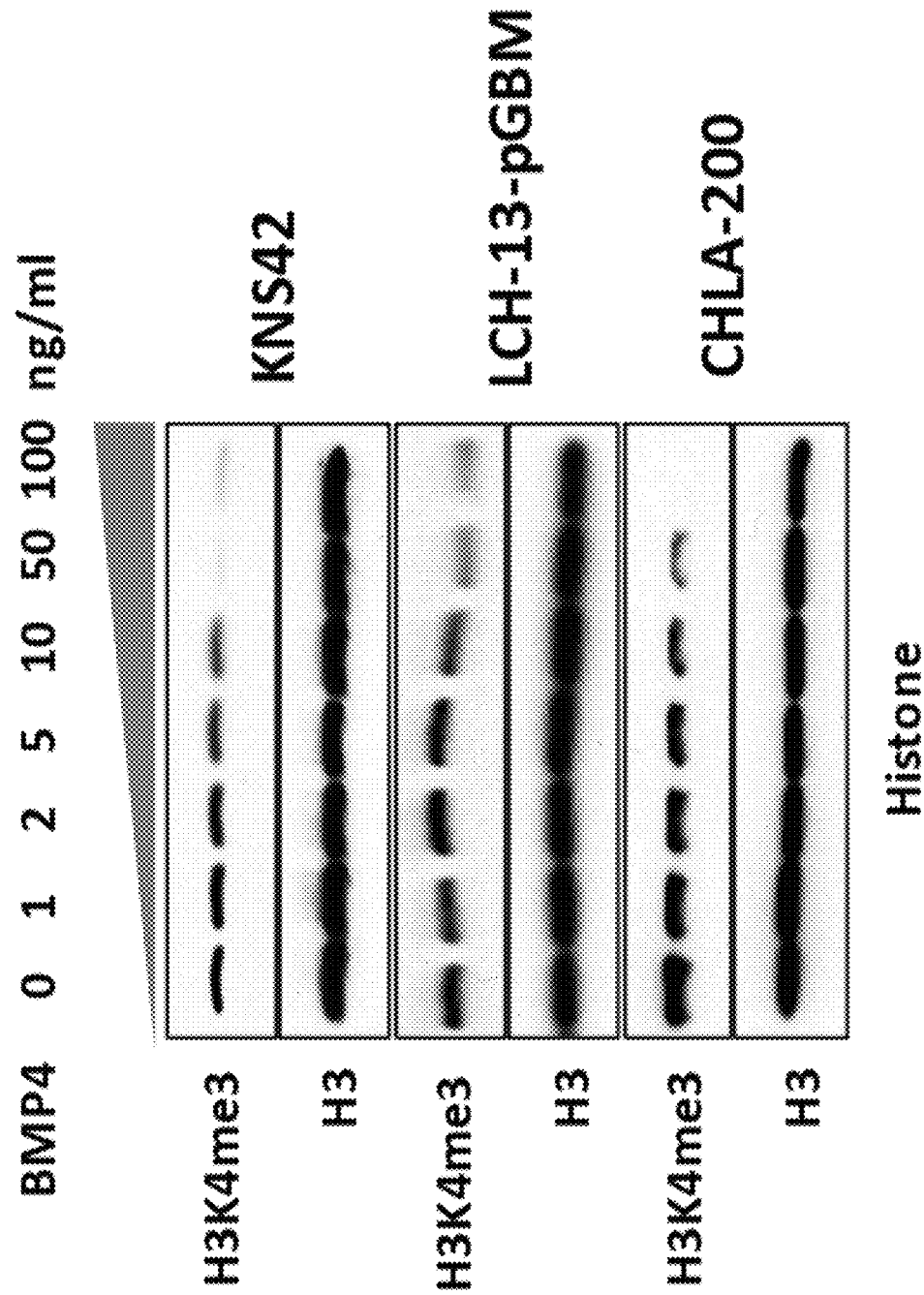
(FIG. 2A) H3K4me3 levels in pediatric high-grade glioma cells in response to BMP4 (1 to 100/ng/ml).
Figure 2B:
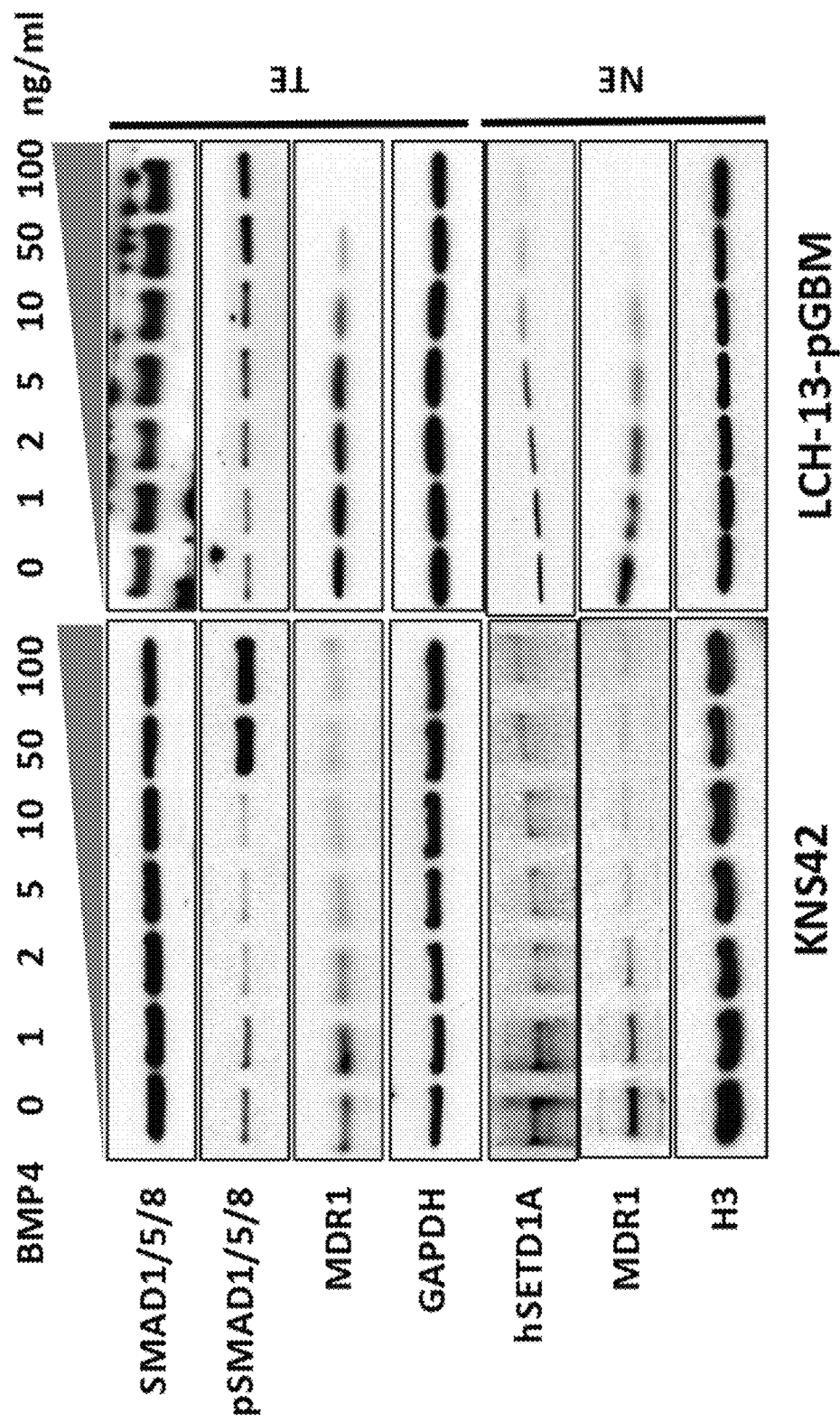
(FIG. 2B) SETD1A, SMAD1/5/8, MDR1, H3K4me3 levels in pediatric high-grade glioma-KNS42 cells and LCH-13-pGBM patient derived primary cultured cells.
Figure 2C:
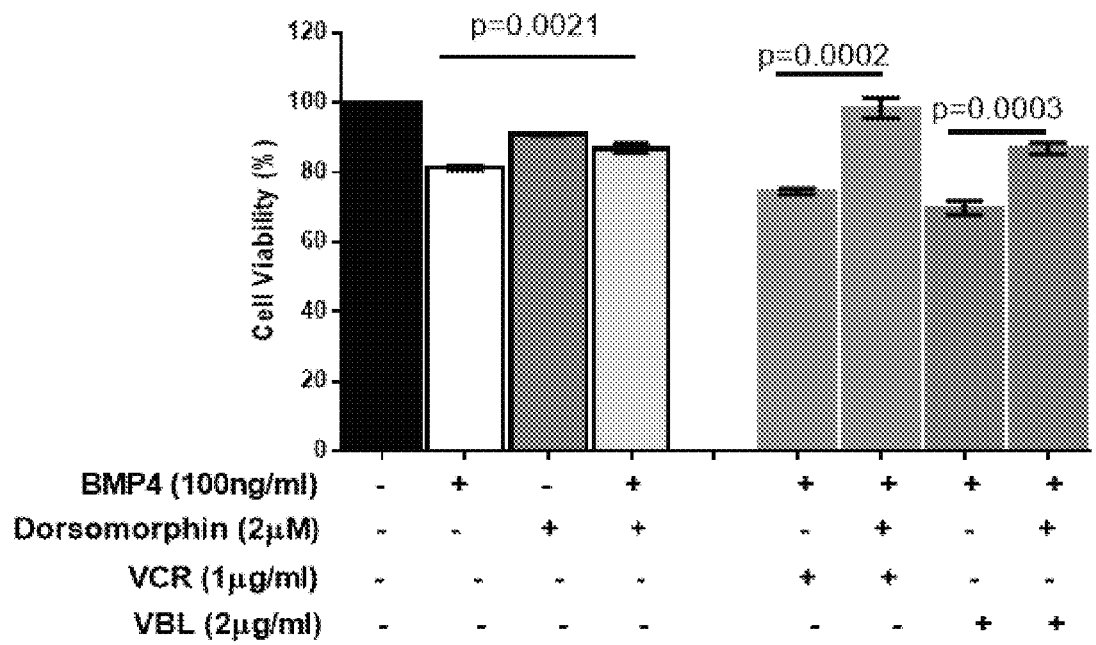
(FIG. 2C) KNS42 cell viability in response to vincristine (VCR) and vinblastine (VBL) with/without Dorsomorphine, a phosphoSMAD1/5/8 inhibitor.
Figure 2C:
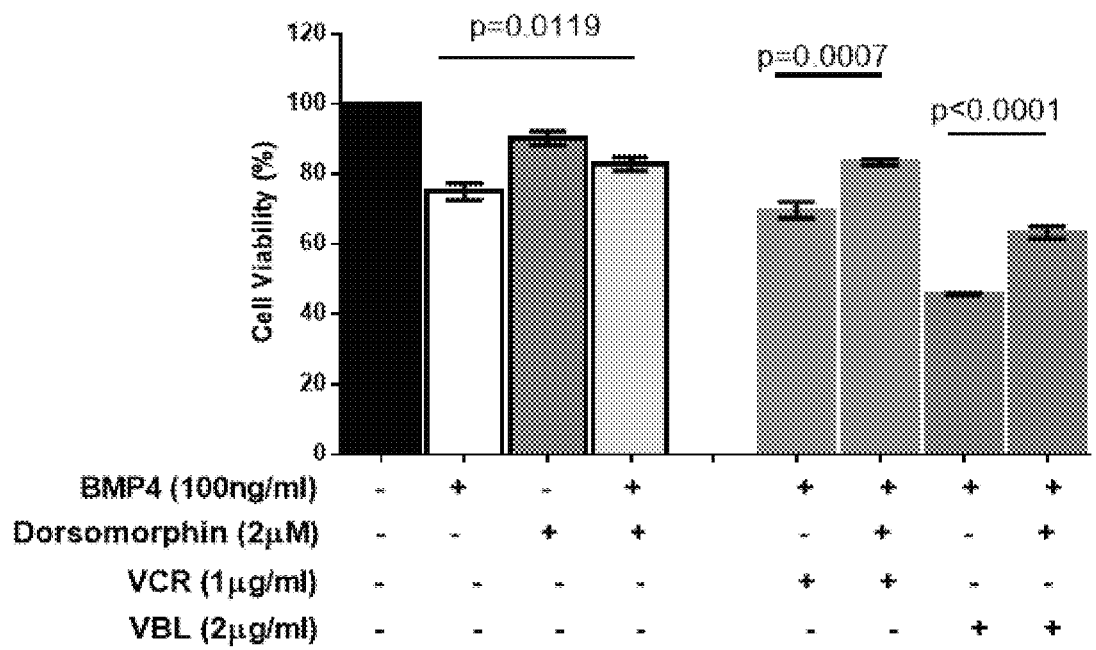
Figure 2D:
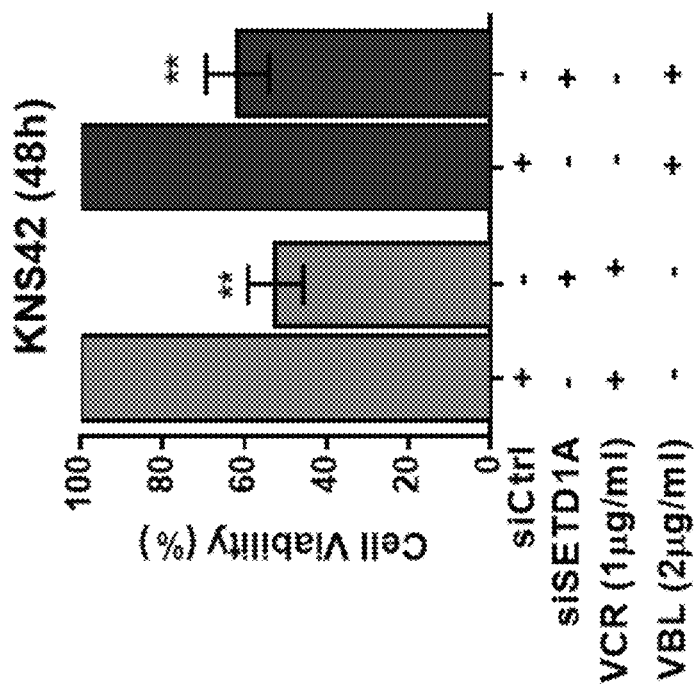
(FIG. 2D, FIG. 2E) KNS42 cell viability in response to VCR and VBL following down- or up-regulation of SETD1A via siSETD1A (D) or pET28-SETD1A and pET28-SETD1A with PSC833, a specific MDR1 inhibitor (E), respectively.
Figure 2E:
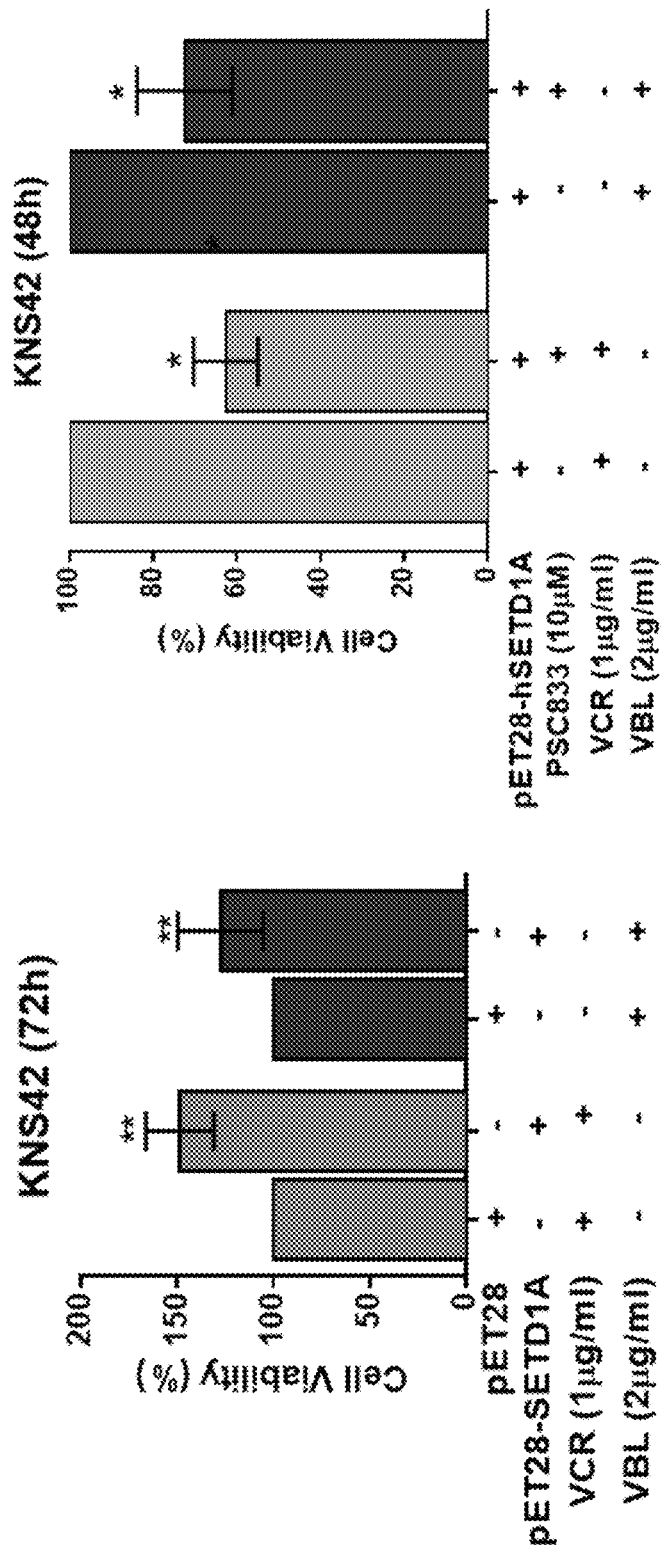
Figure 2F:
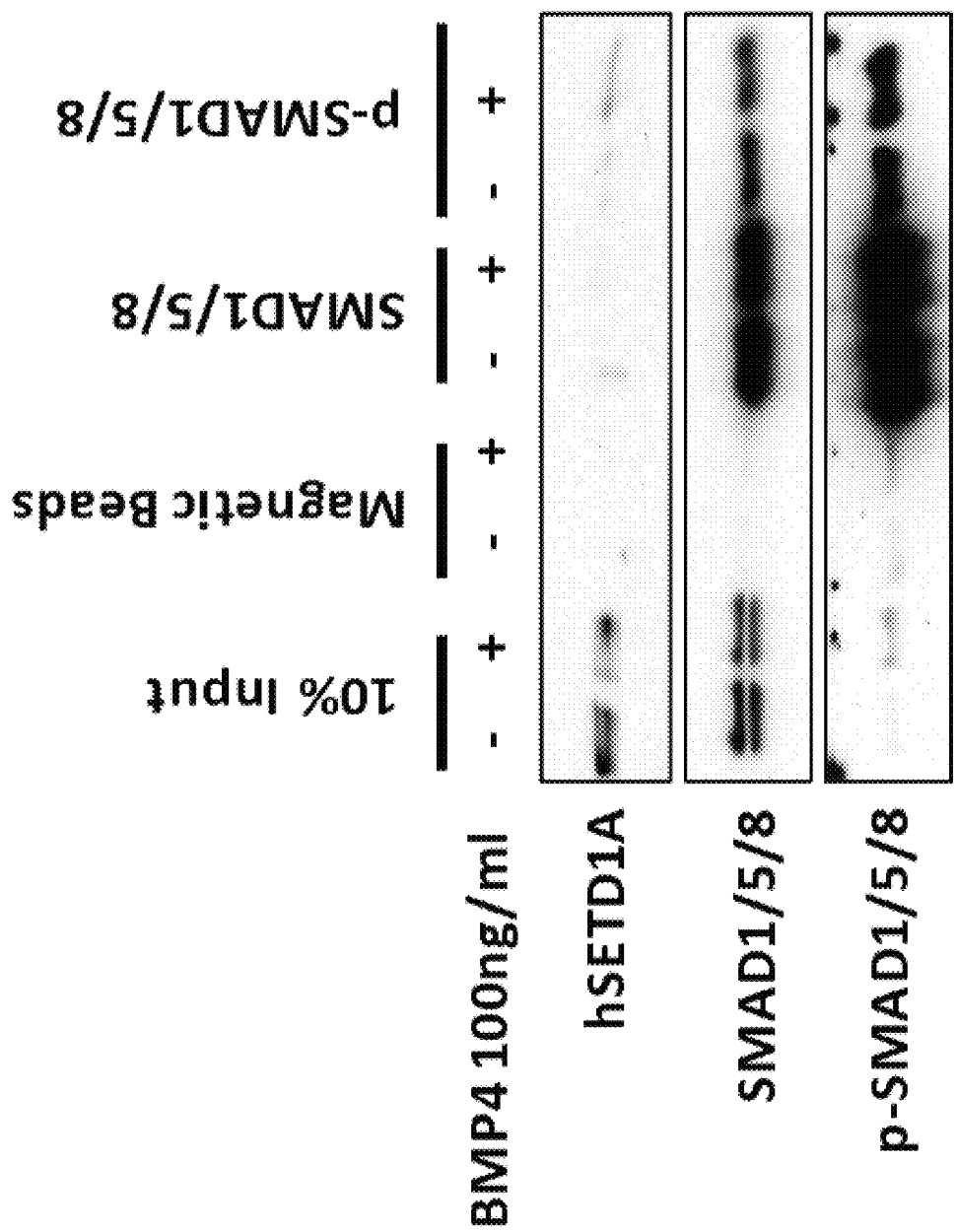
(FIG. 2F) Protein immunoprecipitation with SMAD1/5/8, pSMAD1/5/8 antibodies from total protein extracts from BMP4 treated KNS42 cells using Biotin-streptavidin kit (Thermo Fisher) and detected with SETD1A, SMAD1/5/8, pSMAD1/5/8 using western blots.

BMP4 reduces H3K4me3 through SETD1A. BMP4 signaling reduces H3K4me3 in human neural stem cells, and this finding has been extended to HGG (FIG. 2A). Results also show that BMP4 treatment increases phosphorylation of SMAD1/5/8 (pSMAD1/5/8) while decreasing expression of SETD1A and multidrug resistant gene 1 (MDR1), a key contributor to tumor cell drug resistance (FIG. 2B). When HGG cells are treated with BMP4 for 48 hrs, followed by addition of vincristine (VCR) (1 μg/ml) or vinblastine (VBL) (2 μg/ml), BMP4 markedly decreased cell viability relative to VCR or VBL alone. This decreasing effect is reversed by Dorsomorphine, an inhibitor of pSMAD1/5/8 (FIG. 2C). In parallel, it was also tested and verified that SETD1A is associated with chemosensitivity in vitro in HGG cells (FIGS. 2D and E). Immunoprecipitation results indicate that BMP4 reduces global H3K4me3 by affecting the interaction between pSMAD1/5/8 and SETD1A (FIG. 2F). Thus, it was hypothesized that BMP4 is altering gene expression through its effect on histone PTM. These findings prompted investigation of 1) in addition to H3K4me3, determining other histone PTMs that are affected subsequent to BMP4 treatment of tumor cells; and 2) other gene expression alterations that contribute to the heightened tumor cell response to cytotoxic therapy following BMP4 treatment.

Sulfated heparinopeptide nanostructures augment BMP4 activity, resulting in enhanced pediatric glioma cell chemosensitivity. Preliminary results demonstrate that increasing BMP4 signaling is a potential therapeutic approach for the treatment of HGG. However, there are obstacles that must be overcome for BMP4 to prove an effective therapeutic, including the short half-life of BMP4. Results shown herein reveal that sulfated glycopeptide amphiphile (GlncPA) nanostructures markedly prolong the half-life of BMP4 (FIG. 3). FIG. 3A shows a schematic highlighting the molecular structure of a GlncPA molecule (i.e. the glycosylated peptide amphiphile or "GPA") and a schematic of the self-assembled GlncPA nanofiber. The grey molecular region guides the self-assembly process into nanofibers, the blue molecular region contains the tri-sulfated monosaccharide responsible for protein binding actions. FIG. 3B shows SEM of GlncPA nanofiber bundles after exposure to blood proteins for 5 minutes. FIG. 3C shows higher magnification of nanofibers with white arrows indicating rigid surface texture resulting from proteins binding to the fiber surface.

Figure 3D:
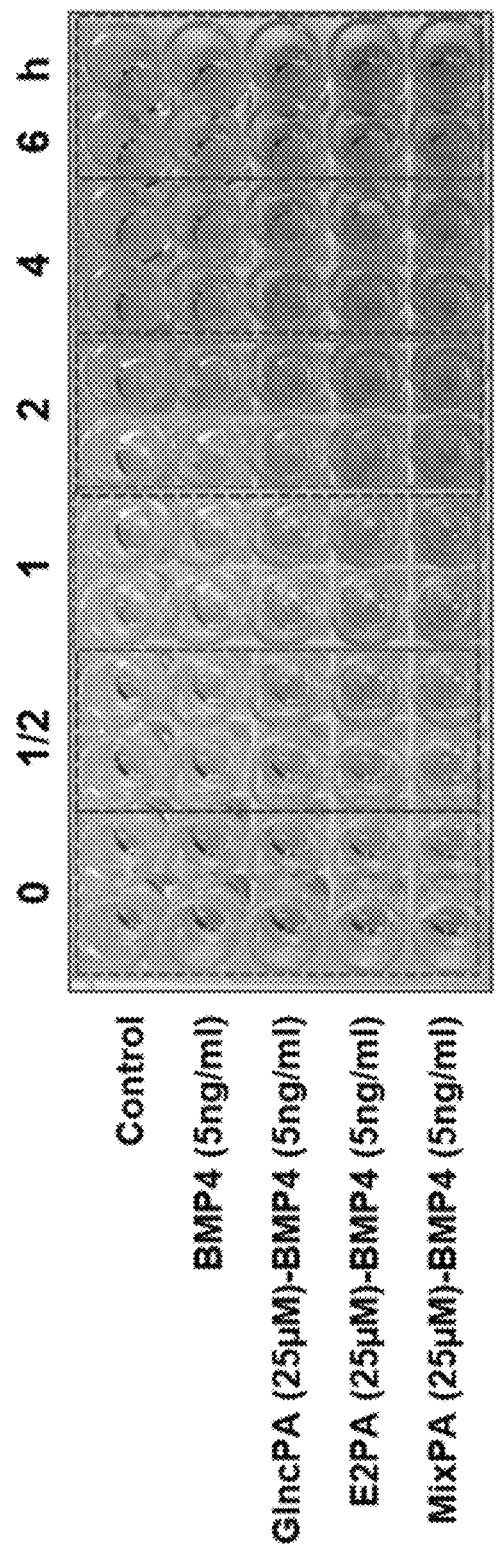
(FIG. 3D, FIG. 3E) ELISA results show that GlncPA, E2-PA, and MixPA (GlncPA+E2PA) extend BMP4 half-life. (Abbreviation: E2PA=filler PA=E2-PA, GlncPA=glycosylated PA=GPA)
Figure 3E:
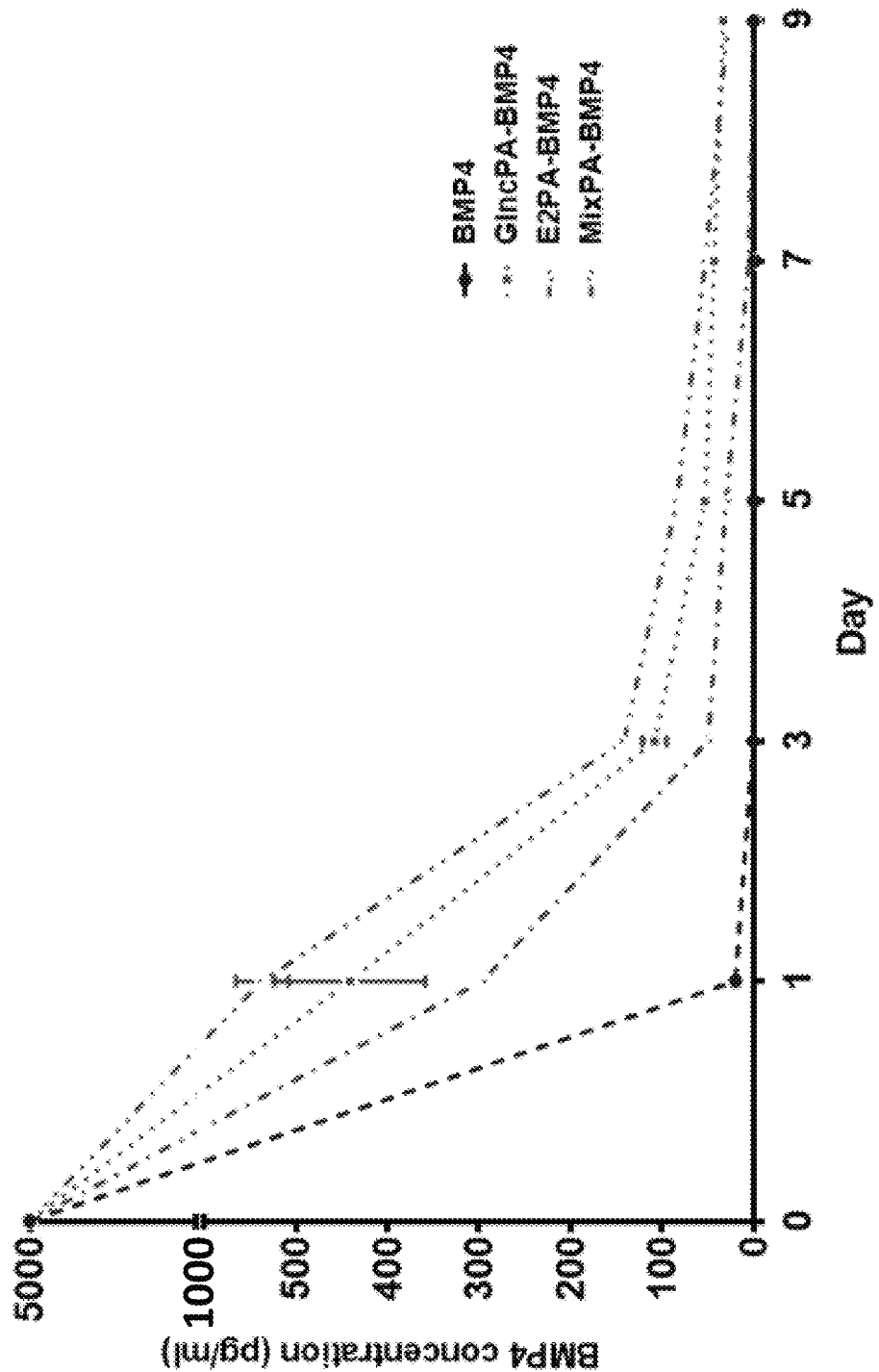

FIG. 3D and FIG. 3E show ELISA results showing that GlncPA, E2-PA, and MixPA (GlncPA+E2PA) extend BMP4 half-life.

Figure 4A:
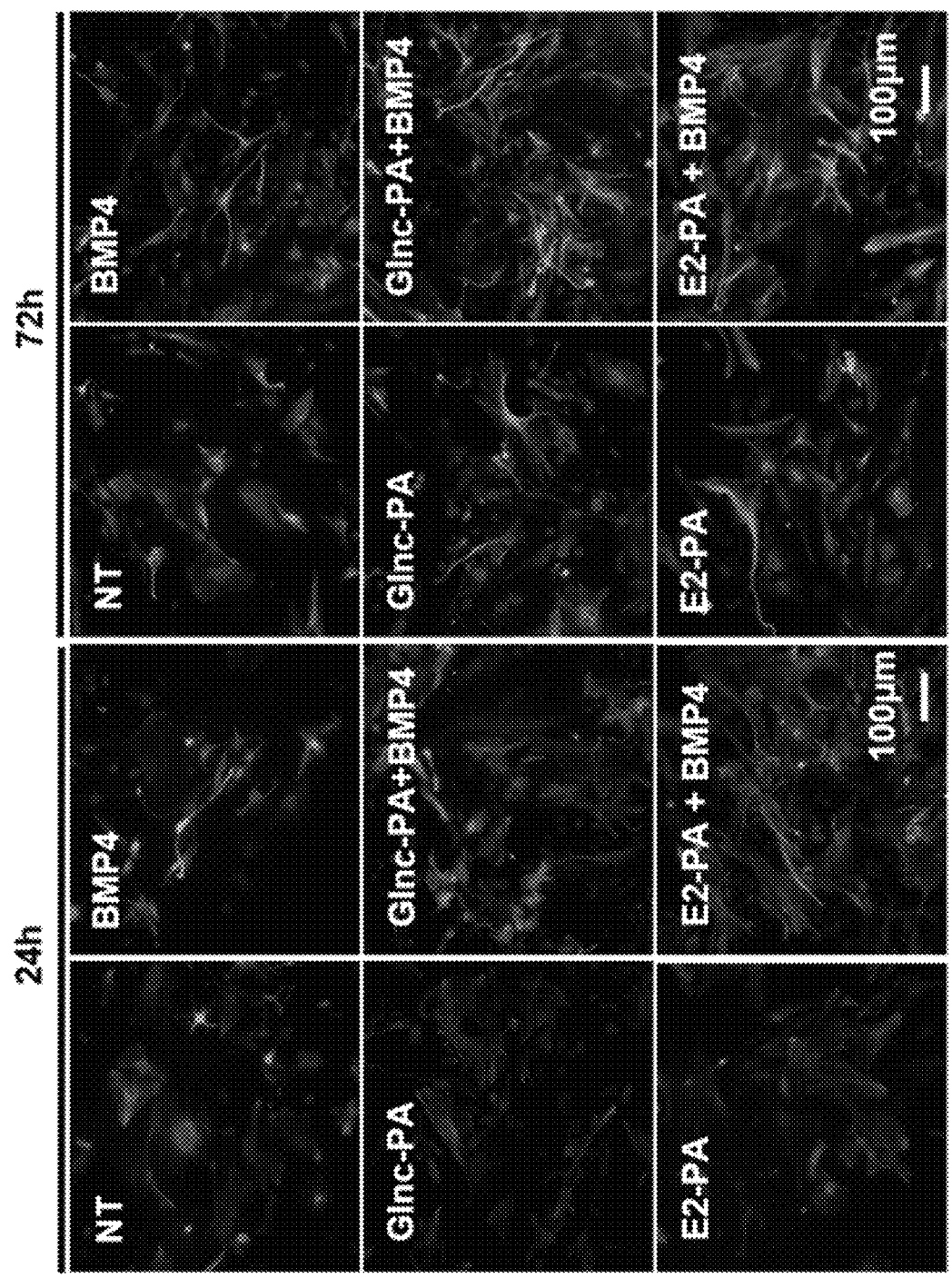
(FIG. 4A) Representative immunofluorescence images of KNS42 pediatric glioblastoma cells treated with BMP4 and peptide amphiphile nanofibers.
Figure 4B:
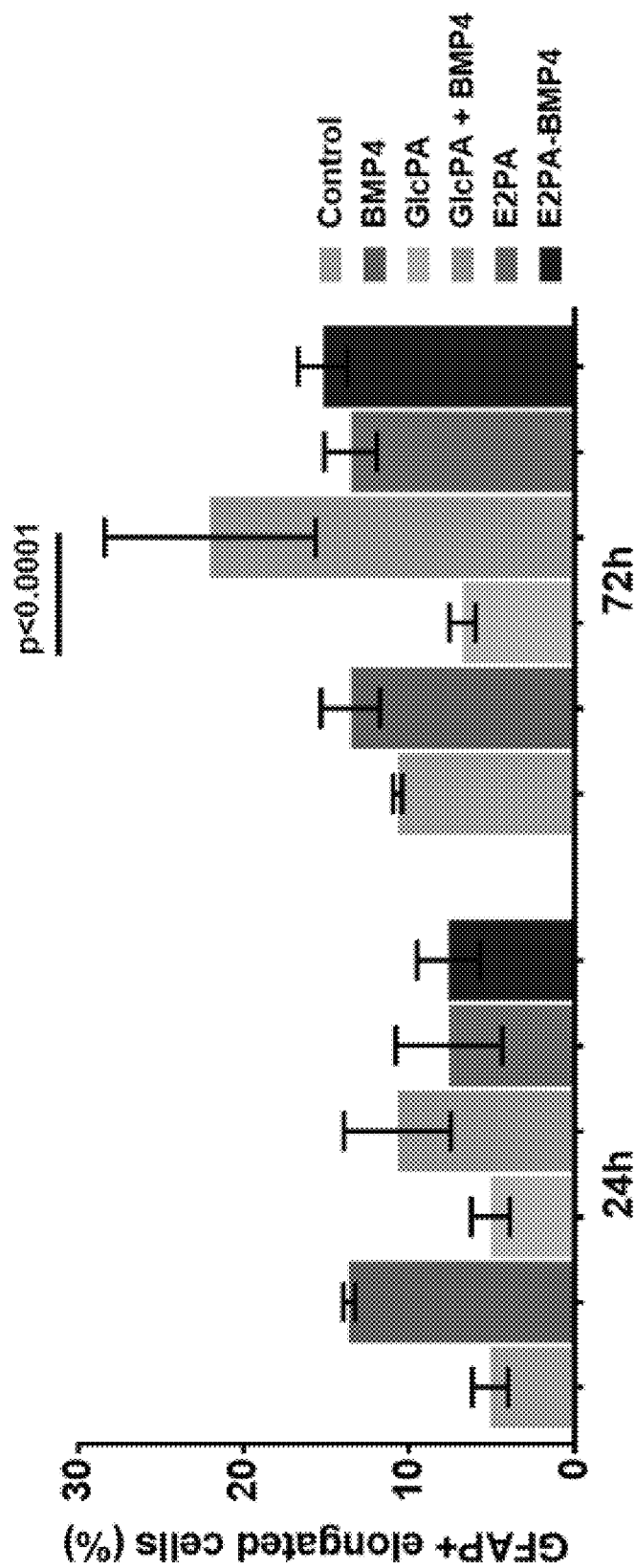
(FIG. 4B) GlncPA+BMP4 markedly increases the elongated GFAP+(astrocyte markers) cell population.
Figure 4C:
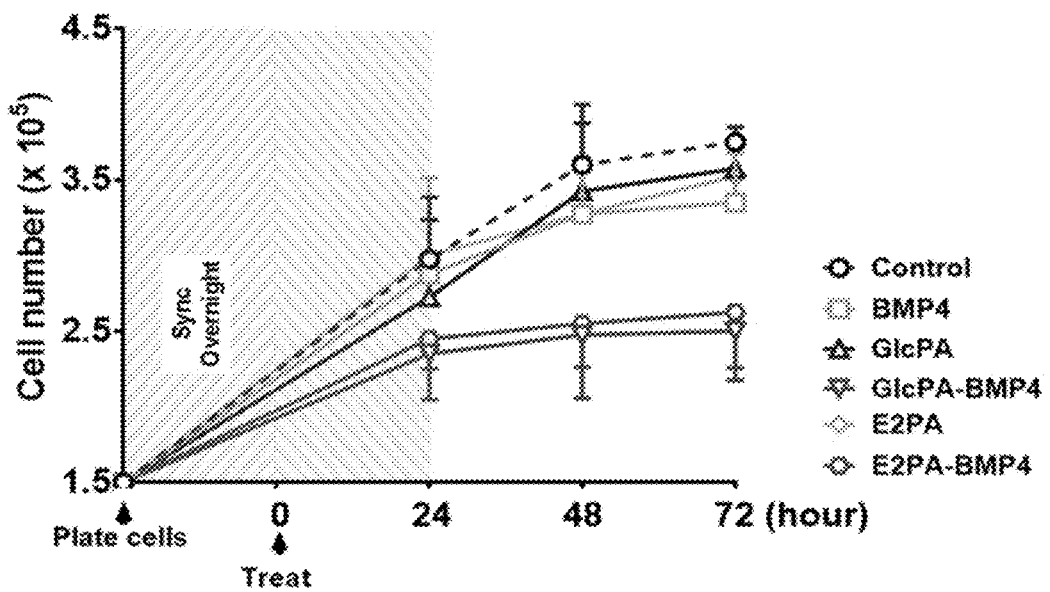
(FIG. 4C) Nanofiber+BMP4 treatments inhibit tumor cell proliferation.
Figure 4D:
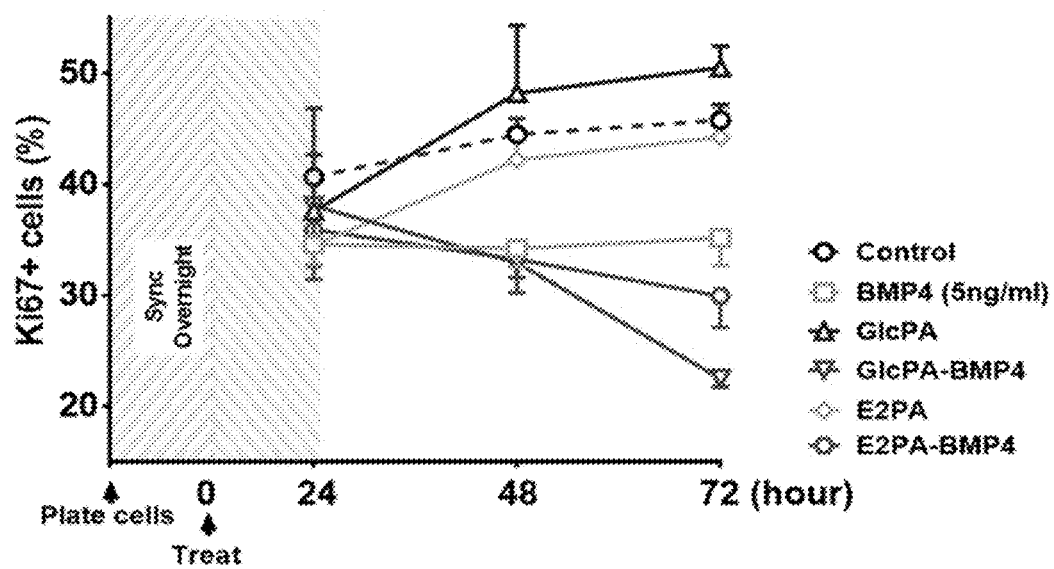
(FIG. 4D) Ki67+marker assay shows Glnc-PA+BMP4 treatment reduces tumor cell proliferation.

Efficacy of BMP4 was further investigated. BMP4 binding peptide amphiphile nanostructures were shown to promote astrocyte differentiation and reduce proliferation. FIG. 4A shows representative immunofluorescence images of KNS42 pediatric glioblastoma cells treated with BMP4 and peptide amphiphile nanofibers. FIG. 4B shows that GlncPA+BMP4 markedly increases the elongated GFAP+(astrocyte markers) cell population. FIG. 4C shows that nanofiber+BMP4 treatment inhibits tumor cell proliferation. FIG. 4D shows a Ki67+marker assay showing that Glnc-PA+BMP4 treatment reduces tumor cell proliferation.

Figure 5A:
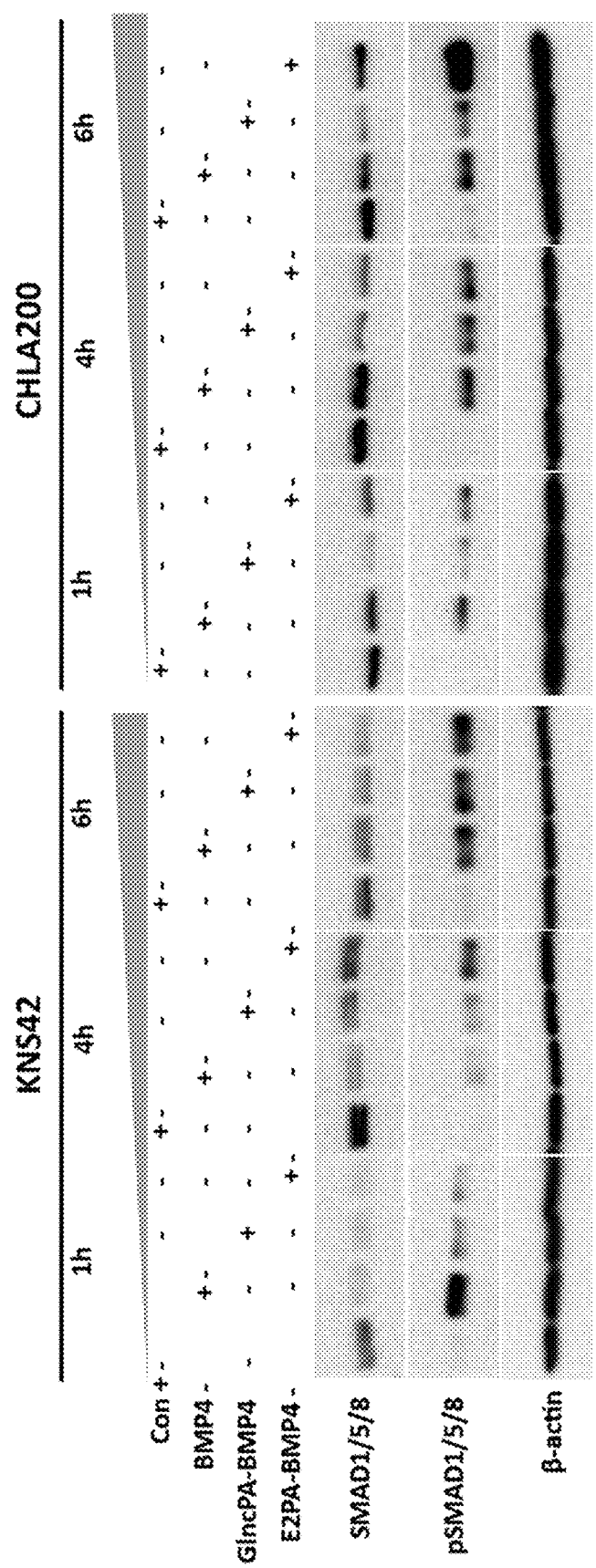
(FIG. 5A) Western blots show PAs enhance BMP4 function by activating its downstream target pSMAD1/5/8 in pediatric glioma KNS42 (FIG. 5B) and CHLA200 cells.
Figure 5B:
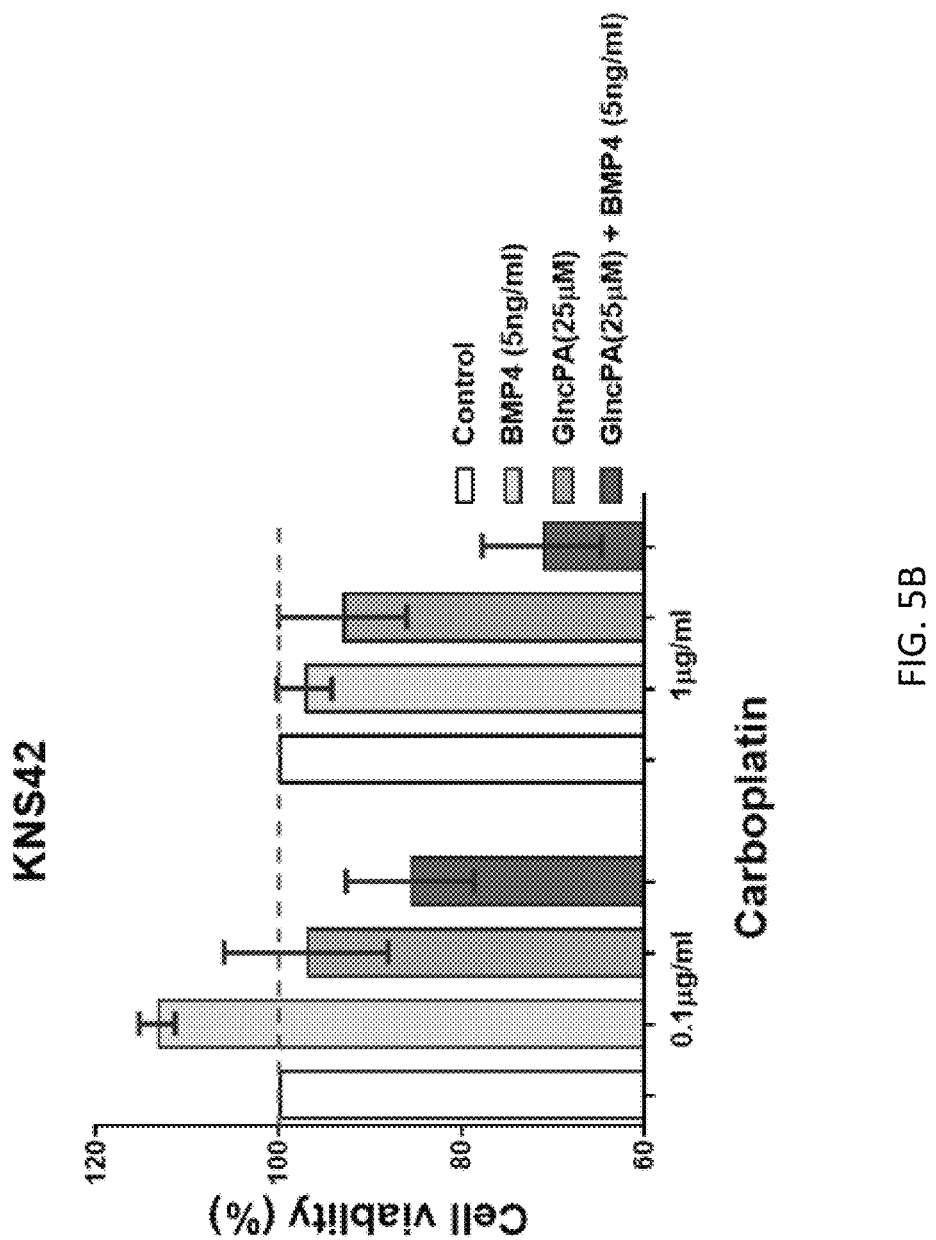
FIG. 5. Self-assembled peptide amphiphile nanostructures extend and enhance BMP4 effects in pediatric high grade glioma cells in vitro.
(FIG. 5C) Increased therapeutic efficacy in response to carboplatin treatment.
Figure 5C:
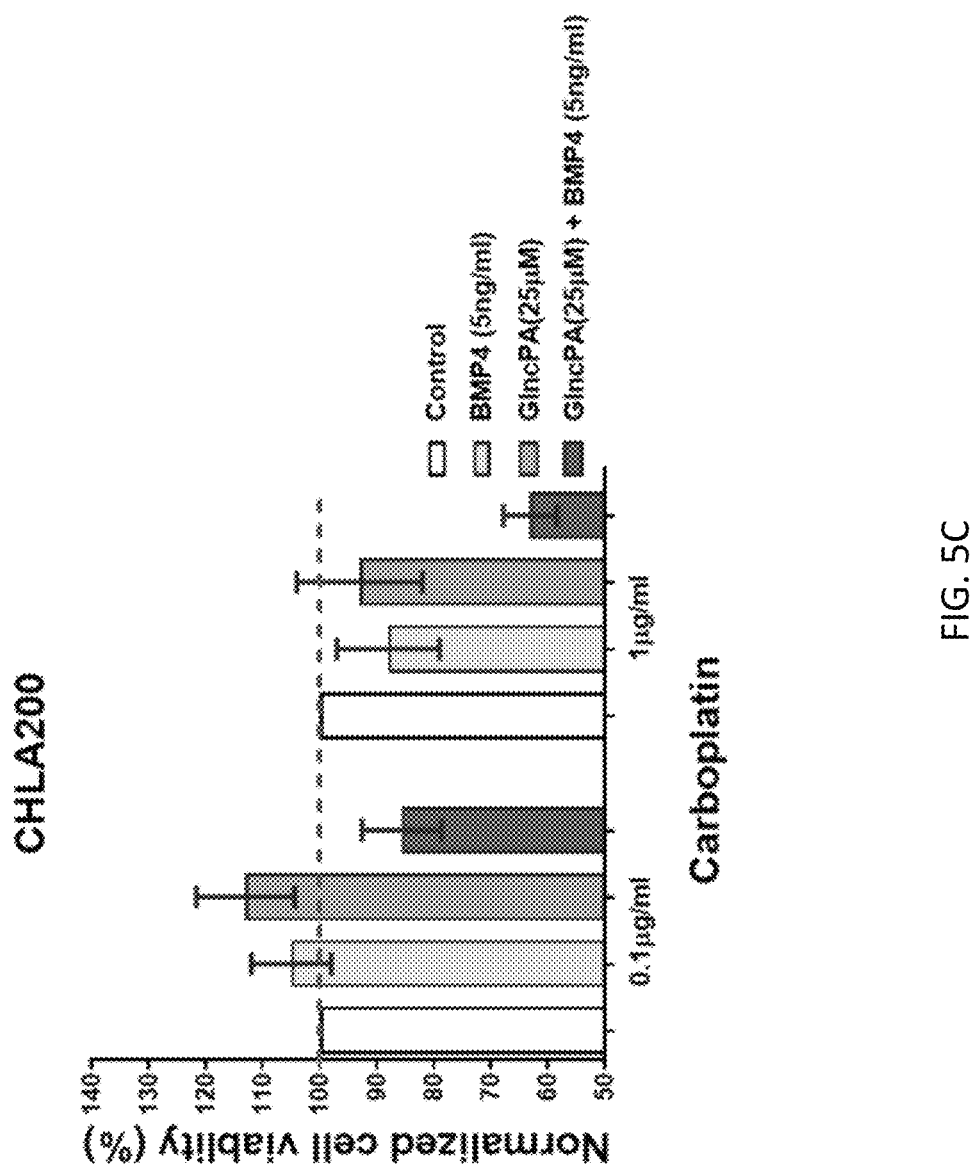

To investigate biological effects of PA-BMP4, HGG responses to different types of PAs, both with and without bound BMP4, were analyzed. HGG cells were treated with BMP4 (5 ng/ml), GlncPA (25 μM) and GlncPA (25 μM)-BMP4 (5 ng/ml), E2-PA (25 μM) and E2-PA (25 μM)-BMP4 (5 ng/ml) for 24h and 72h. Western blot results showed that both GlncPA and E2-PA enhance BMP4 activity, as indicated by extended phosphorylation of the BMP4 downstream target, SMAD1/5/8 (FIG. 5A) and increased HGG cell chemosensitivity (FIG. 5B, FIG. 5C).

Sulfated glycopeptide nanostructures binding BMP4 reduces pediatric HGG tumor growth. Intracranial distribution of PAs administered directly into mouse brain, as well as the anti-tumor activity of direct intratumoral administration of PA-bound BMP4, was investigated.

Figure 6A:
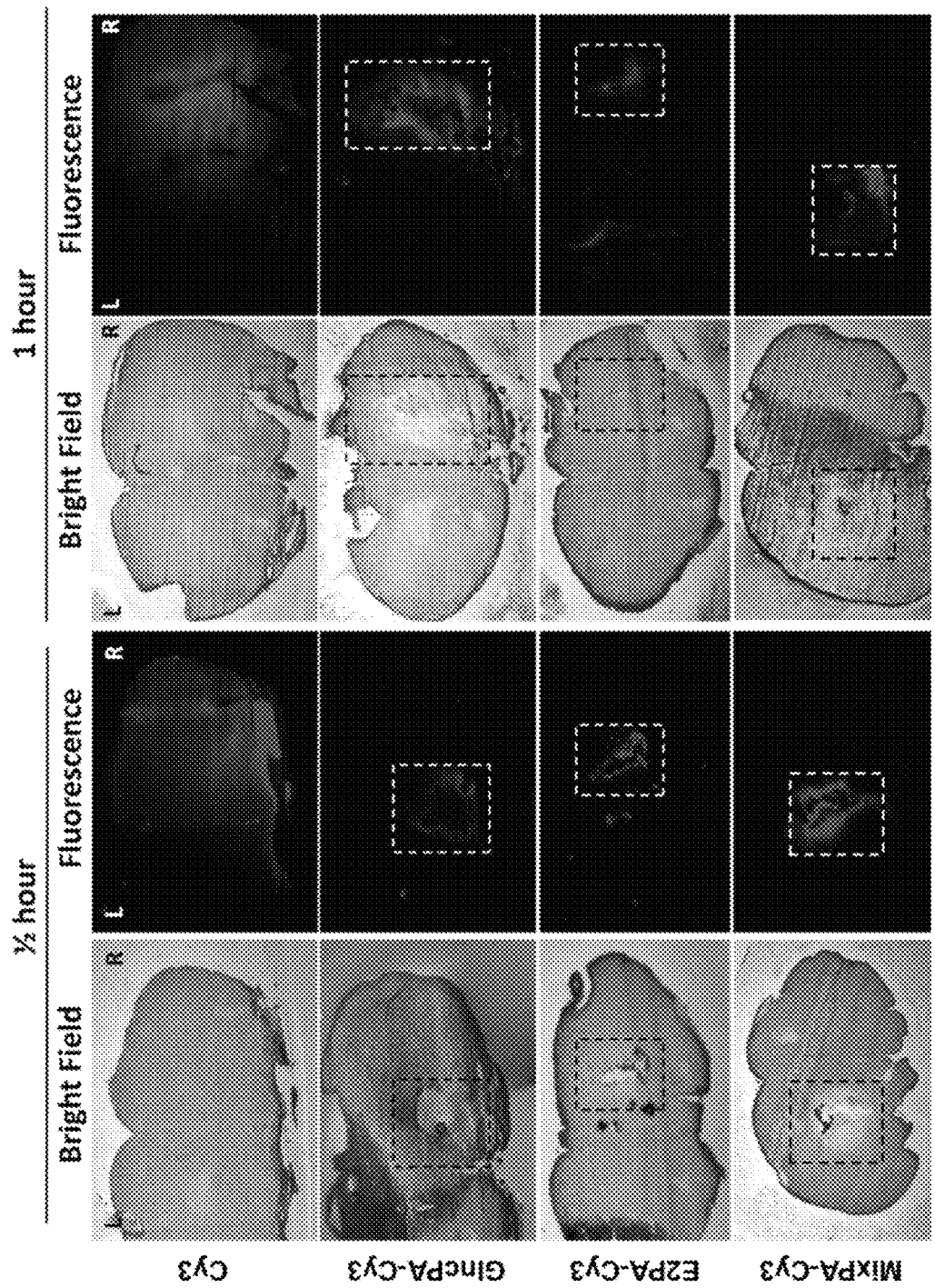
(FIG. 6A) Intracranial distribution of glycosylated (GlncPA), E2 (E2PA) and glycosylated+E2 (MixPA) peptide amphiphiles coupled with Cy3. The results showed GlncPA has greater distribution following intracranial injection.
Figure 6B:
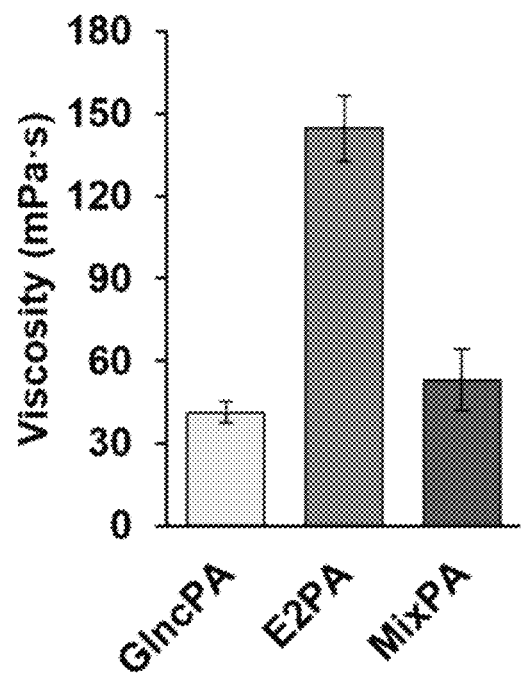
(FIG. 6B) Viscosity of PA nanofiber solutions.
Figure 6C:
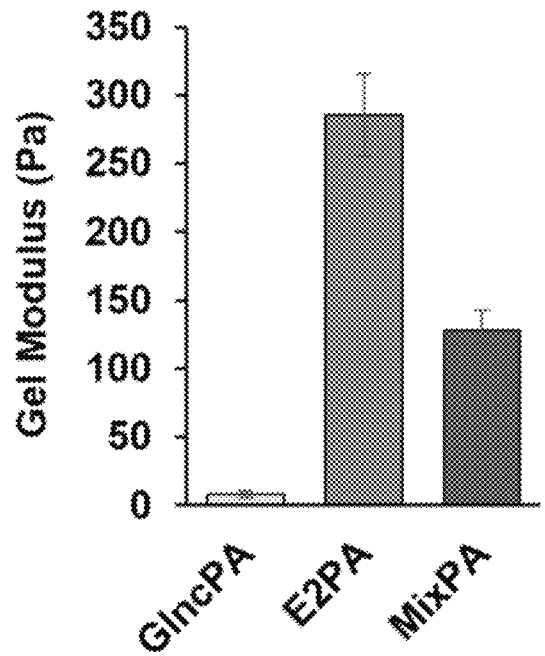
(FIG. 6C) Gel storage modulus (G') of nanofiber implants treated with 2.5 mM $CaCl_2$) and 150 mM NaCl to mimic cerebrospinal fluid ion concentration.

Peptide amphiphile nanostructures were shown to spread to cover larger area in orthotopic xenograft intracranial tumor models. FIG. 6A shows intracranial distribution of glycosylated (GlncPA), E2 (E2PA) and glycosylated+E2 (MixPA) peptide amphiphiles coupled with Cy3. The results showed GlncPA has greater distribution following intracranial injection due to lower viscosity and gel modulus. FIG. 6B shows the viscosity of PA nanofiber solutions. FIG. 6C shows the gel storage modulus (G') of nanofiber implants treated with 2.5 mM $CaCl_2$) and 150 mM NaCl to mimic cerebrospinal fluid ion concentration.

Figure 7A:
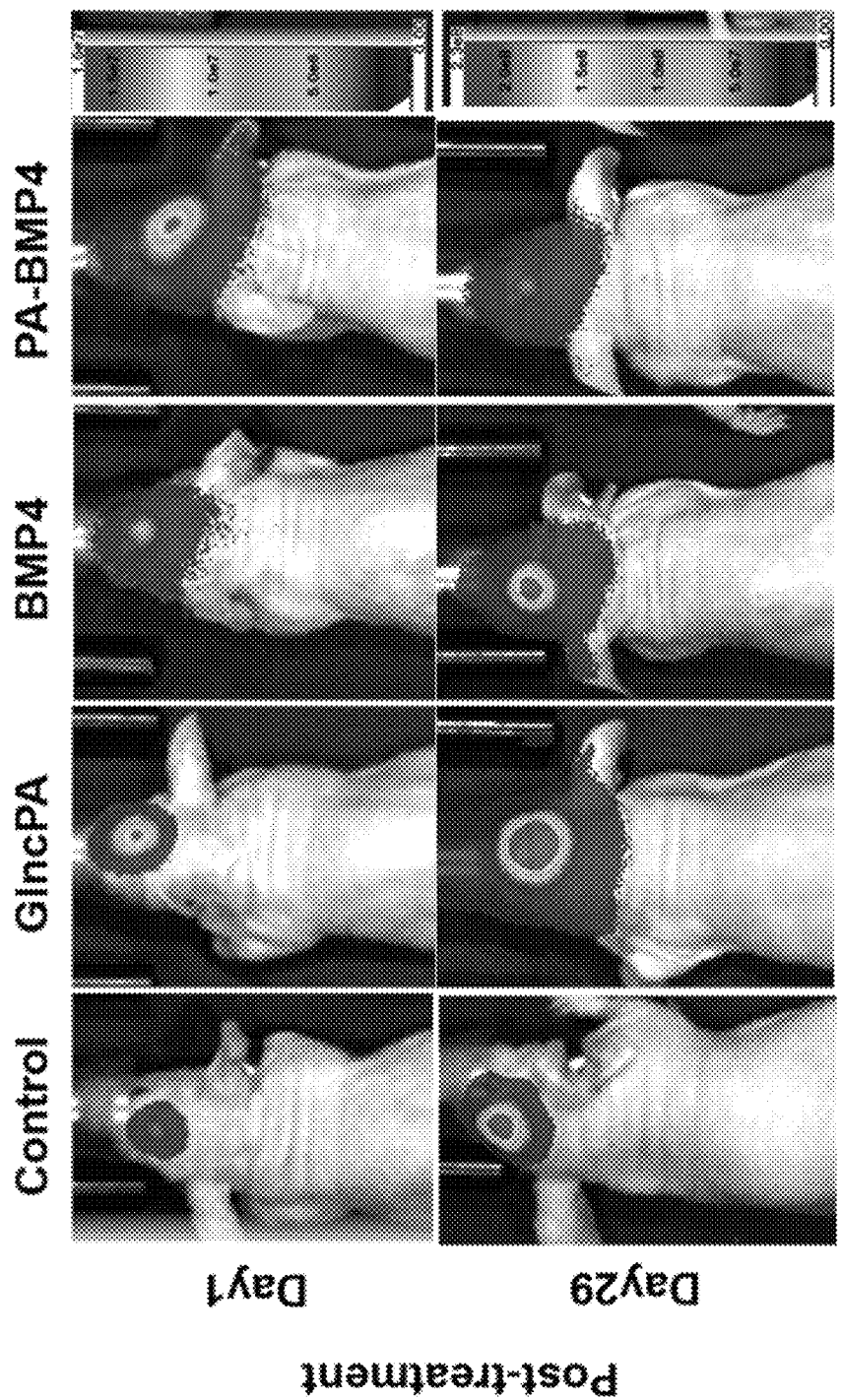
(FIG. 7A) Representative images of bioluminescence intensity of KNS42 xenograft tumors in nude mice for various treatments.
Figure 7B:
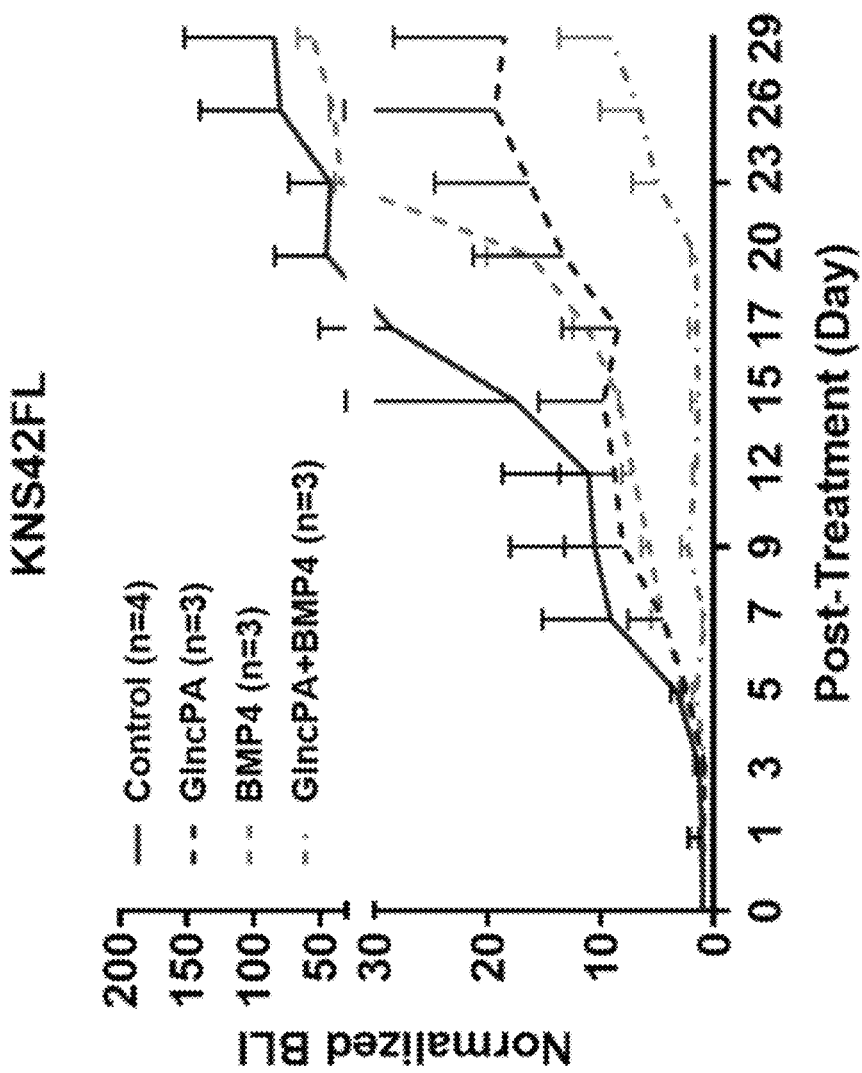
(FIG. 7B) Quantitative bioluminescence intensity showing GlncPA-BMP4 markedly decreases pediatric high-grade glioma KNS42 tumor growth.
Figure 7C:
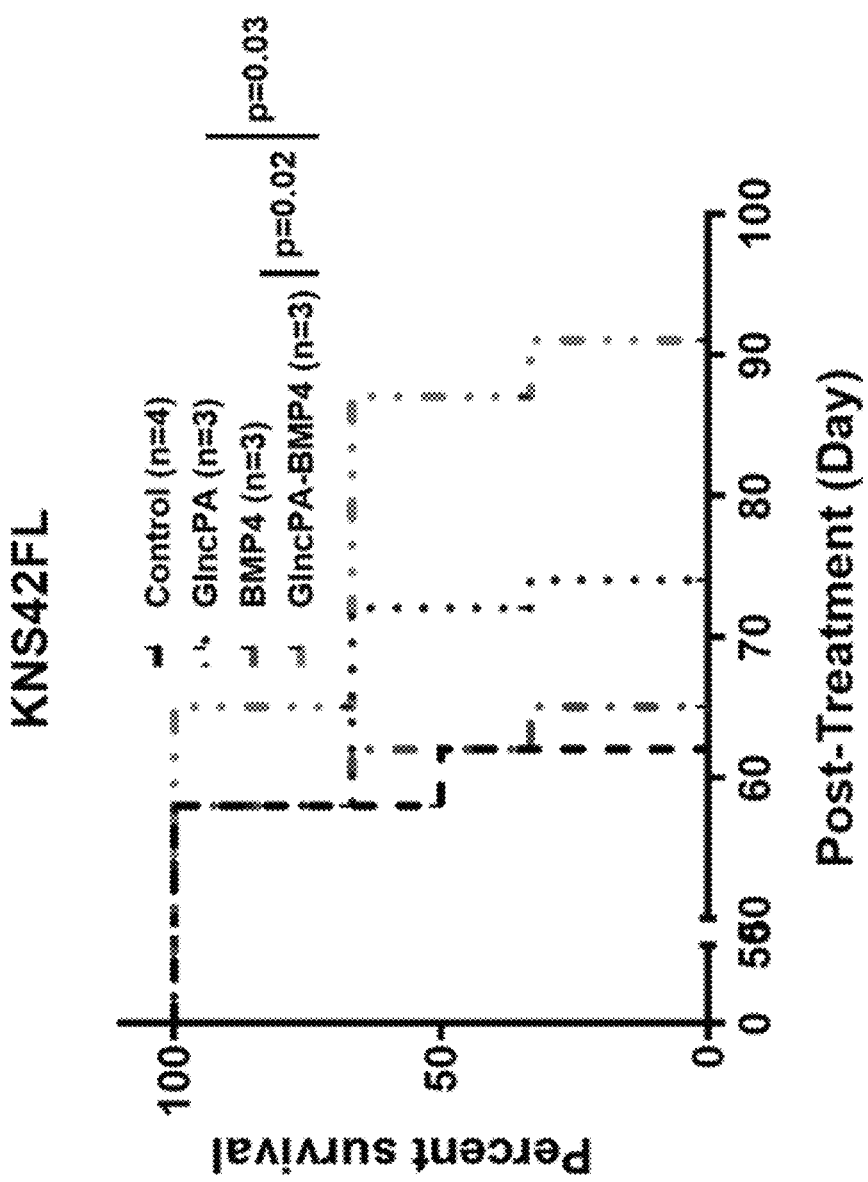
(FIG. 7C) Survival curves show GlncPA-BMP4 treatment increases survival in vivo.

FIG. 7 shows that glycosylated peptide amphiphile nanostructures decrease tumor growth in vivo in orthotopic xenograft intracranial tumor models. FIG. 7A shows representative images of bioluminescence intensity of KNS42 xenograft tumors in nude mice for various treatments. FIG. 7B shows quantitative bioluminescence intensity showing GlncPA-BMP4 markedly decreases pediatric high-grade glioma KNS42 tumor growth. FIG. 7C shows survival curves showing that GlncPA-BMP4 treatment increases survival in vivo.

Figure 8A:
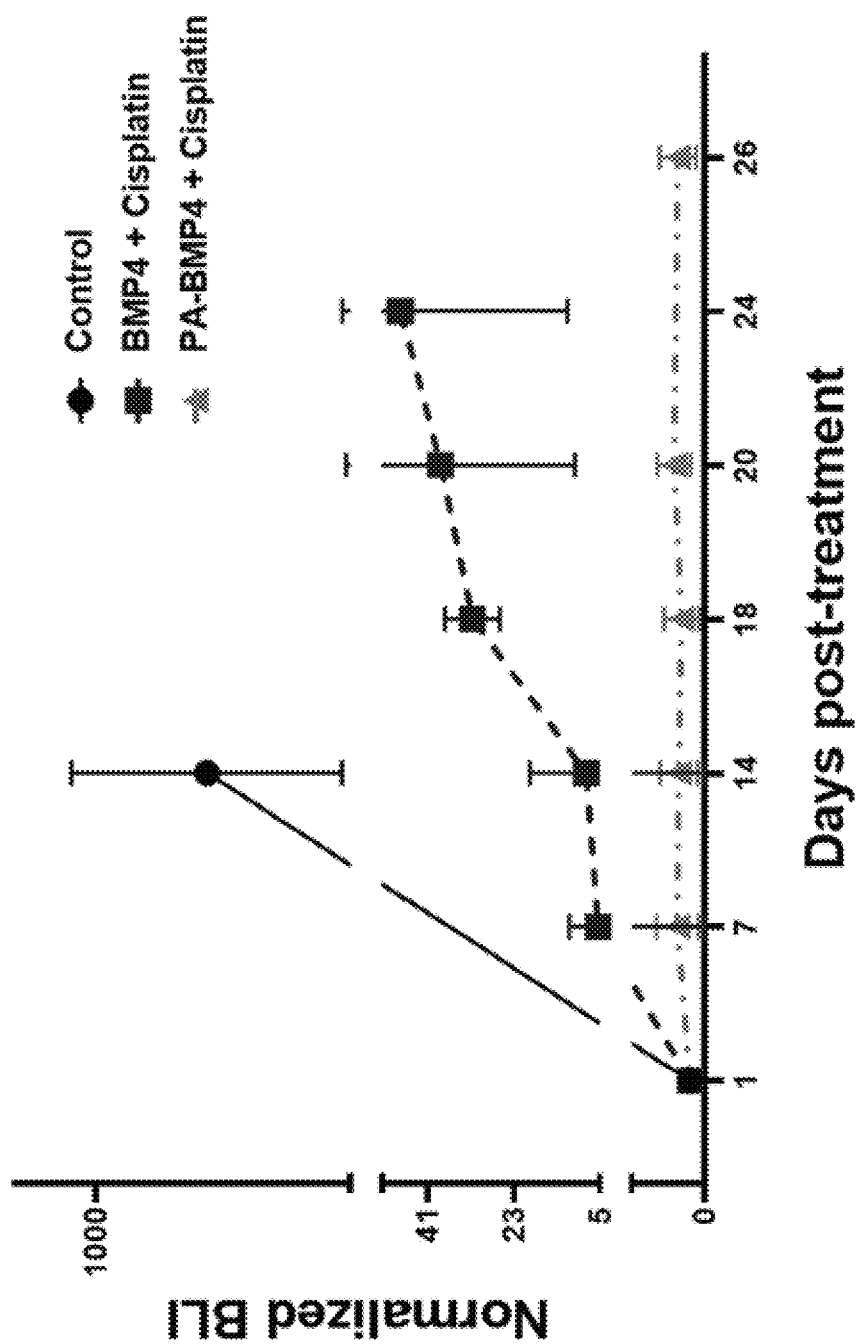
(FIG. 8A) Quantitative bioluminescence intensity for KNS42 tumors treated with 33 ng of BMP4 and 3 μg of cisplatin (BMP4+cisplatin) and 33 ng BMP4 delivered with glycosylated PA nanofibers and 3 μg cisplatin (PA-BMP4+cisplatin).
Figure 8B:
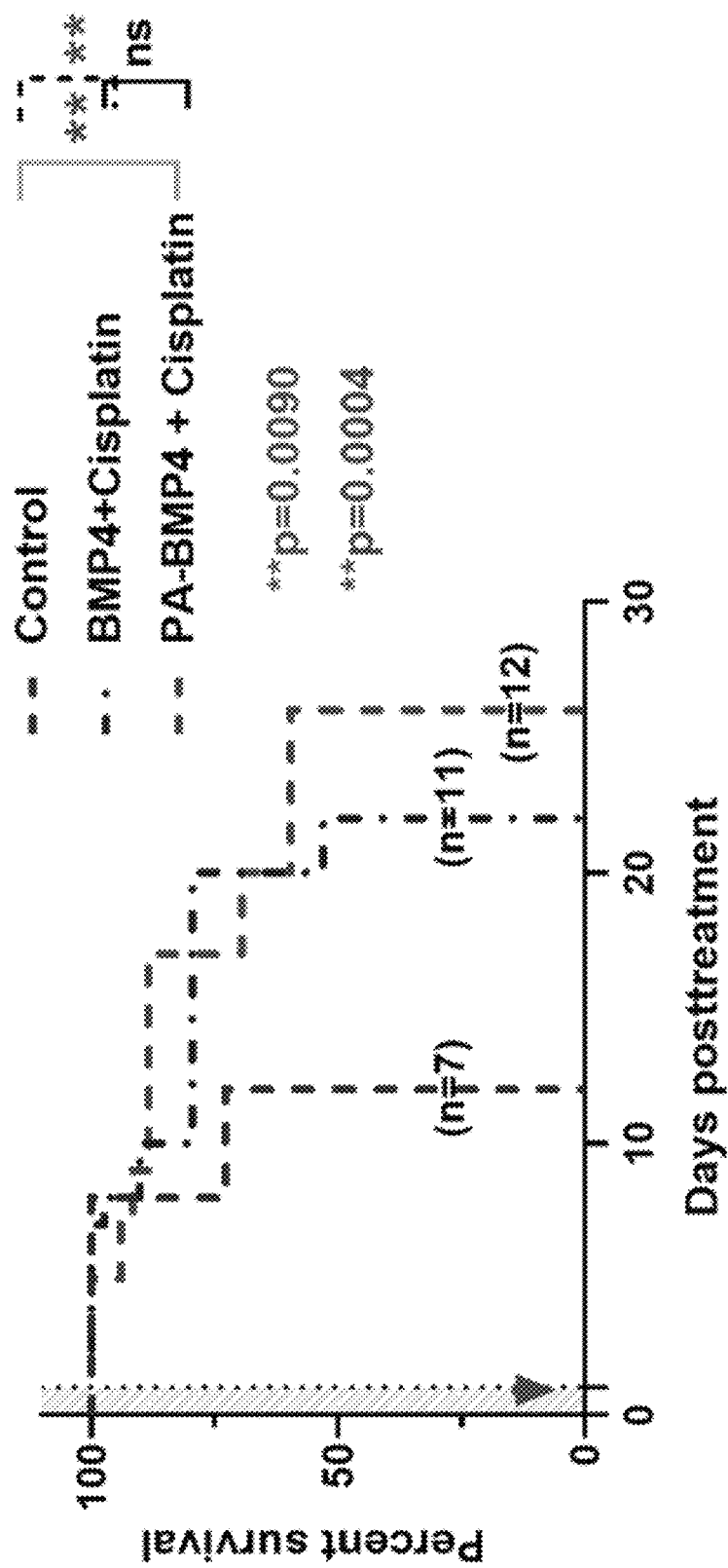
(FIG. 8B) Survival analysis of SCID mice for each treatment shows prolonged BMP4 signaling with GlncPA enhances chemosensitivity and survival in vivo.

FIG. 8. shows that glycosylated peptide amphiphile nanostructures enhance chemosensitivity and increase survival of SCID mice treated with chemotherapy drug. FIG. 8A shows quantitative bioluminescence intensity for KNS42 tumors treated with 33 ng of BMP4 and 3 μg of cisplatin (BMP4+cisplatin) and 33 ng BMP4 delivered with glycosylated PA nanofibers and 3 μg cisplatin (PA-BMP4+cisplatin). FIG. 8B shows survival analysis of SCID mice for each treatment shows prolonged BMP4 signaling with GlncPA enhances chemosensitivity and survival in vivo.

Overall, these results demonstrate that BMP4 alters histone H3K4 methylation and causes a change in the expression of a gene involved with drug resistance. The results further demonstrate the use of GlncPA, as novel BMP4 delivery platforms, for reduction of tumor growth and enhanced survival in vivo.

Example 2

Further evaluation of histone H3 PTMs DNA repair gene expression may be evaluated, such as in association with BMP4-induced changes. Luciferase-modified pediatric HGG xenograft models may be used to evaluate BMP4 sulfated BMP4 binding glycopeptide nanostructures anti-tumor activity, with and without chemotherapy and radiation therapy co-treatment.

Characterize Histone Alterations Associated with DNA Repair Gene Expression Following Treatment of Pediatric HGG Cells with BMP4:

These studies will identify changes in histone PTM and gene expression changes that are associated with heightened therapeutic response in pediatric HGGs following BMP4 treatments.

For these studies, histones and RNA may be extracted from HGG cells treated with BMP4. Treatment-associated changes in H3 PTM, including for methylation and acetylation changes to H3 K4, K9, K27, and K34 may be examined by western blot. RNAs may be analyzed by whole transcriptome RNAseq, with RNAseq results for genes involved with DNA repair further examined by quantitative PCR. DNA repair protein expression may be examined by western blot, with western blot results compared with corresponding PCR results. It is hypothesized that BMP4 acts to alter histone PTMs, and that PTM changes influence tumor cell transcription programs, including for genes whose encoded proteins are involved with DNA repair.

Histone: Histone alterations may be analyzed following BMP4 treatment of pediatric HGG cell lines CHLA-03-AA, UW479 and SF7795 (WHO grade III) and SJ-GBM2, CHLA-200, SF9427 and KNS42 (WHO grade IV) (26). Histones may be extracted from tumor cell nuclei and examined on western blots. BMP4-induced changes in histone PTM modifier and DNA repair protein expression will be similarly examined.

RNA-Seq: Gene expression profiles may be determined through RNA-Seq analysis. Total RNA may be extracted from treated and untreated HGG cells. RNA quality may be determined prior to library construction. Barcoded RNA-Seq next-generation sequence (NGS) libraries may be prepared using the Illumina TruSeq Stranded RNA-seq library preparation kit, as described at www.illumina.com. Three replicates per tissue/cell line may be sequenced (50 bp single-end) using the Illumina HiSeq 4000 with approximately 25 million reads per sample. After sequencing, the quality of reads, in FASTQ format, may be evaluated using FastQC. Adapters may be trimmed and reads of poor quality or aligning to rRNA sequences may be filtered. The cleaned reads will be aligned to the *H. sapiens* genome (hg38) using STAR. Read counts for each gene may be calculated using HTseq-count in conjunction with a gene annotation file for hg38 obtained from UCSC (http://genome.ucsc.edu). Differential gene expression may be determined using DESeq2. The cutoff for determining genes which show significant differential expression will be an FDR-adjusted p-value<0.05.

Chromatin immunoprecipitation coupled with next-generation sequencing (ChIP-Seq): To identify genes associated with specific histone marks, chromatin may be immunoprecipitated with ChIP grade antibodies for specific histone PTMs, such as H3K4me3 and H3K27me3, etc. followed by NGS of immunoprecipitated DNA. Enriched DNA may be used to construct sequencing libraries using the Illumina TruSeq ChIP Library Preparation Kit. Libraries may be sequenced (50 bp single-end) using the Illumina HiSeq 4000 with approximately 25 million reads per sample. After sequencing, the quality of reads, in FASTQ format, may be evaluated using FastQC. Adapters may be trimmed; reads of poor quality may be filtered. The cleaned reads may be aligned to the *H. sapiens* genome (hg38) using Bowtie (30). Peak calling and differential peak analysis may be performed using HOMER (http://homer.ucsd.edu/homer/index.html).

Integrative analysis of RNA-seq and ChIP-Seq data: Potential DNA damage response candidate genes whose expression is affected by BMP4 may be identified by integrative analysis of RNA- and ChIP-Seq data, in association with the NUSeq Core Facility. ChIP-Seq data may be projected upon the RNA-Seq data to determine the extent to which genes located in the vicinity of histone marks are differentially expressed.

Validation of integrative analyzed results: Candidate gene expression may be validated at transcriptional and translational levels using real-time PCR and western blot analysis, respectively. Relationships between candidate genes and identified histone marks may be validated with ChIP-PCR array. Cell lines described above may be used to support this analysis.

Quantitative Milestones: Both RNA and protein results are expected to reveal histone PTMs that are significantly altered following BMP4 treatment. For RNA-Seq, gene expression verified ≥2-fold change may be selected for integrative analysis with ChIP-seq. Determination of protein expression changes may be based on band intensity comparisons of western blot results.

Comparison of BMP4 treated and untreated control cells may lead to the identification of candidate genes whose expression are likely linked with HGG chemotherapeutic and radiation sensitivity. Further, BMP4-induced changes of such genes may be associated with changes of specific H3 PTMs, as well as with changes in the expression of effectors/modifiers of specific H3 PTMs. For example, preliminary results show a significant decrease in H3K4me3 following treatment with BMP4. Histone modifiers associated with this mark, include methyltransferases hKMT2A-H, hKDM7, hKDM1 and hKDM5A-D, and corresponding gene expression changes may be identified for at least some of these modifiers. This would indicate that BMP4 H3 PTM effects are not limited to K4, and such knowledge is likely to implicate additional H3 modifiers as therapeutic targets for treating HGG. Some H3 PTMs are known to often be linked, or bivalent. For example, H3K4me3 and H3K27me3 often occur together. If these two PTMs are identified, histone modifiers associated with these marks, for example hKMT1C and hKMT6, may be investigated. If clearly bivalent histone marks and their modifiers are not identified, then cross-talk among active and inactive histone marks, and their localization to candidate genes associated with chemotherapeutic and radiation sensitivity, may be further investigated.

Test the efficacy of BMP4-binding supramolecular nanofibers with/without cytotoxic therapies when administered to mice bearing orthotopic HGG xenografts: Outcomes from recent attempts to treat human gliomas with BMP4 have been largely unsuccessful, with the relatively short in vivo half-life of BMP4 thought to be the primary factor. Novel BMP4 delivery platforms are needed in order for BMP4 to prove a useful cancer therapy.

The BMP4-PA platform is based on the self-assembly of PA nanofibers into gel scaffolds. Gel scaffolds carrying BMP4 can disseminate through brain to activate BMP4 receptors on tumor cells. A major advantage of this system is the extension of BMP4 in vivo activity.

Luciferase-modified pediatric malignant glioma models. HGG cell lines KNS42, SJ-GBM2 and SF9975 and SF9427 may be tested. All lines are modified for stable expression of luciferase and are tumorigenic. Cell suspensions may be prepared from HGG cell cultures as described above and then injected intracranially in athymic mice ($1-3\times10^5$ luciferase transduced cells per mouse). Tumor growth and response to treatment may be monitored twice weekly by bioluminescence imaging (BLI). All animals may be monitored for the length of survival.

BMP4-PA adjuvant to chemo- and radiation therapy in the treatment of mice with intracranial HGG orthotropic xenograft models. Intracranial glioma bearing mice may be treated with control (0.9% saline), BMP4 and BMP4-PA, with/without first-line clinical chemotherapy drugs vincristine and carboplatin to investigate therapeutic efficacy as indicated by monitoring tumor bioluminescence intensity (BLI) and determining length of animal survival.

Quantitative Milestones: For BLI, data from each treatment group may be collected and used to plot normalized bioluminescence values at each imaging time-point. Brains from mice may be resected and processed for immunohistochemical analysis of treatment effects on tumor cell proliferation and apoptotic response.

BMP4-PA nanofiber/scaffolds, compared to PAs or free BMP4, may promote greater tumor cell apoptotic response when used in the presence of chemotherapeutic agents and irradiation. BMP4-PA used in combination with chemotherapy and irradiation may confer the most substantial survival benefit to animal subjects. The proposed volume of BMP4 and PAs, and dose of chemotherapeutic drugs and radiation may be selected based on literature the results from Example 1. If initial BMP4-PA+cytotoxic/genotoxic therapy treatments indicate excessive toxicity, as determined by animal subject condition from treatment (e.g., rapid weight loss), the amount of chemotherapeutic drug and/or radiation may be reduced.

The invention claimed is:

1. A method of treating glioma in a subject, comprising providing to the subject a composition containing:
   (a) a plurality of glycosylated peptide amphiphiles (GPAs), wherein each GPA comprises a hydrophobic segment, a structural peptide segment, a charged peptide segment, and a terminal saccharide, and
   (b) a bone morphogenic protein, wherein the bone morphogenic protein is BMP-4, wherein the plurality of GPAs are configured to form a self-assembled glyconanostructure, and wherein the bone morphogenic protein binds to the surface of the glyconanostructure.

2. The method of claim 1, wherein the saccharide is selected from a monosaccharide, disaccharide, oligosaccharide, and a glycomimetic.

3. The method of claim 1, wherein the saccharide is chemically functionalized with one more groups selected from sulfates, sulfonates, phosphates, phosphonates, quaternary ammonium, and heterocycles.

4. The method of claim 1, wherein the saccharide is sulfated.

5. The method of claim 1, wherein the saccharide is selected from:
(a) the monosaccharides consisting of GlcA, GlcNAc, GlcNS, IdoA, Glc, Gal, Man, Tal, GlcN, GalNAc, GalNH$_2$, Fru, Neu5Ac, Fuc, Rha, Xyl, Rib, Ara, and sulfated versions thereof;
(b) disaccharides of GlcA, GlcNAc, GlcNS, IdoA, Glc, Gal, Man, Tal, GlcN, GalNAc, GalNH$_2$, Fru, Neu5Ac, Fuc, Rha, Xyl, Rib, Ara, and sulfated versions thereof;
(c) oligosaccharides of GlcA, GlcNAc, GlcNS, IdoA, Glc, Gal, Man, Tal, GlcN, GalNAc, GalNH$_2$, Fru, Neu5Ac, Fuc, Rha, Xyl, Rib, Ara, and sulfated versions thereof;
(d) glycomimetics;
(e) sulfated fucoidan disaccharides and oligosaccharides; and
(f) sugar alcohols and polyols.

6. The method of claim 1, wherein the composition further comprises a chemotherapeutic agent, or wherein the method further comprises providing to the subject a chemotherapeutic agent.

7. The method of claim 6, wherein the chemotherapeutic agent is an alkylating agent or an alkylating-like agent.

8. The method of claim 1, wherein the composition further comprises one or more filler peptide amphiphiles (PAs), wherein the one or more filler PAs comprise a hydrophobic segment, a structural peptide segment, and a charged peptide segment, but lack a terminal saccharide, and wherein the one or more filler PAs are configured to assemble into the glyconanostructure.

9. The method of claim 1, wherein the glioma is a brain cancer.

10. The method of claim 9, wherein the brain cancer is pediatric high grade glioma.

11. The method of claim 1, wherein the composition is provided to the subject intracranially.

* * * * *

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Ala Ala Val Val
1

<210> SEQ ID NO 2
<211> LENGTH: 6
<212> TYPE: PRT
<213> ORGANISM: Artificial Sequence
<220> FEATURE:
<223> OTHER INFORMATION: Synthetic

<400> SEQUENCE: 2

Ala Ala Ala Val Val Val
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Gln Gln Lys Phe Gln Phe Gln Phe Glu Gln Gln
1               5                   10
```